(12) United States Patent
Jacobson et al.

(10) Patent No.: US 8,615,293 B2
(45) Date of Patent: Dec. 24, 2013

(54) CARDIOELECTROMAGNETIC TREATMENT

(75) Inventors: Jerry I. Jacobson, Jupiter, FL (US);
Benjamin J. Scherlag, Oklahoma City, OK (US); William S. Yamanashi, Edmond, OK (US)

(73) Assignee: Jacobson Resonance Enterprises, Inc., Boynton Beach, FL (US)

( * ) Notice: Subject to any disclaimer, the term of this patent is extended or adjusted under 35 U.S.C. 154(b) by 481 days.

(21) Appl. No.: 11/711,524

(22) Filed: Feb. 27, 2007

(65) Prior Publication Data

US 2007/0276440 A1    Nov. 29, 2007

Related U.S. Application Data

(62) Division of application No. 10/682,131, filed on Oct. 9, 2003, now Pat. No. 7,186,209.

(51) Int. Cl.
*A61N 2/02* (2006.01)
*A61N 2/04* (2006.01)
*A61N 1/05* (2006.01)

(52) U.S. Cl.
USPC .................................... 607/2; 607/9

(58) Field of Classification Search
USPC .................... 607/65, 2, 9; 600/9–15
See application file for complete search history.

(56) References Cited

U.S. PATENT DOCUMENTS

| | | | |
|---|---|---|---|
| 781,448 A | 1/1905 | McIntyre | |
| 2,099,511 A | 1/1934 | Caesar | |
| 2,103,440 A | 4/1934 | Weissenberg | |
| 3,738,369 A | 6/1973 | Adams et al. | |
| 3,890,953 A | 6/1975 | Kraus et al. | |
| 3,967,215 A | 6/1976 | Bellak | |
| 4,047,068 A | 9/1977 | Ress et al. | |
| 4,323,056 A | 4/1982 | Borrelli et al. | |
| 4,524,079 A | 6/1985 | Hofmann | |

(Continued)

FOREIGN PATENT DOCUMENTS

| | | |
|---|---|---|
| AU | B-45680/89 | 6/1990 |
| EP | 37 1 504 | 1/1997 |

(Continued)

OTHER PUBLICATIONS

Adey, W.R., "Physiological Signaling Across Cell Membranes and Cooperative Influences of Extremely Low Frequency Electromagnetic Fields," *Biological Coherence and Response to External Stimuli*, Herbert Frohlich Ed., Springer-Verlag, 1988, 148-170.

(Continued)

*Primary Examiner* — Rex R Holmes
*Assistant Examiner* — Christopher A Flory
(74) *Attorney, Agent, or Firm* — Kilpatrick Townsend & Stockton LLP

(57) ABSTRACT

Disclosed are methods of treatment or prophylaxis of a disease state or a condition ameliorated or prevented by electromagnetic field application. A person having or susceptible to such disease state or condition is subjected to electromagnetic fields having a frequency between zero and about 200 Hertz. The diseased state or condition may include diseased heart valves, an enlarged heart, circulatory blockage, coronary insufficiencies, and ischemia. The treatment may be administered non-invasively or invasively. An implantable device for invasively administering the treatment may include at least one component emitting electromagnetic fields having a frequency between zero and about 200 Hertz. The component may include at least one inductor.

8 Claims, 11 Drawing Sheets

(56) References Cited

U.S. PATENT DOCUMENTS

| | | | |
|---|---|---|---|
| 4,576,172 | A | 3/1986 | Bentall |
| 4,611,599 | A | 9/1986 | Bentall et al. |
| 4,674,481 | A | 6/1987 | Boddie et al. |
| 4,950,221 | A * | 8/1990 | Gordon ............................ 600/12 |
| 5,019,076 | A | 5/1991 | Yamanashi |
| 5,170,784 | A | 12/1992 | Ramon et al. |
| 5,198,181 | A | 3/1993 | Jacobson |
| 5,269,746 | A | 12/1993 | Jacobson |
| 5,366,435 | A | 11/1994 | Jacobson |
| 5,453,072 | A | 9/1995 | Anninos et al. |
| 5,470,846 | A | 11/1995 | Sandyk |
| 5,496,258 | A | 3/1996 | Anninos et al. |
| 5,691,324 | A | 11/1997 | Sandyk |
| 5,691,325 | A | 11/1997 | Sandyk |
| 5,697,883 | A | 12/1997 | Anninos et al. |
| 5,706,813 | A * | 1/1998 | Filler et al. .................... 600/422 |
| 5,885,976 | A | 3/1999 | Sandyk |
| 5,964,759 | A | 10/1999 | Yamanashi |
| 6,004,257 | A | 12/1999 | Jacobson |
| 6,022,479 | A | 2/2000 | Smirnov |
| 6,059,781 | A | 5/2000 | Yamanashi |
| 6,099,459 | A | 8/2000 | Jacobson |
| 6,123,724 | A * | 9/2000 | Denker ......................... 623/3.11 |
| 6,132,360 | A | 10/2000 | Halpern |
| 6,280,376 | B1 | 8/2001 | Holcomb |
| 6,287,614 | B1 | 9/2001 | Peiffer |
| 6,458,071 | B1 | 10/2002 | Jacobson |
| 6,579,375 | B2 | 6/2003 | Beckett et al. |
| 6,690,971 | B2 * | 2/2004 | Schauerte et al. ............. 607/17 |
| 6,733,434 | B2 | 5/2004 | Jacobson |
| 6,853,864 | B2 * | 2/2005 | Litovitz ........................ 607/100 |
| 6,899,667 | B2 * | 5/2005 | Becker et al. .................... 600/9 |
| 6,917,833 | B2 | 7/2005 | Denker et al. |
| 7,186,209 | B2 | 3/2007 | Jacobson et al. |
| 2002/0026222 | A1 | 2/2002 | Schauerte et al. |
| 2002/0026228 | A1 | 2/2002 | Schauerte |
| 2003/0171640 | A1 * | 9/2003 | Canedo ............................ 600/9 |
| 2004/0181115 | A1 | 9/2004 | Sandyk et al. |
| 2004/0199210 | A1 * | 10/2004 | Shelchuk ........................ 607/17 |
| 2005/0153885 | A1 * | 7/2005 | Yun et al. ........................ 514/12 |

FOREIGN PATENT DOCUMENTS

| | | |
|---|---|---|
| EP | 1 036 574 | 9/2000 |
| EP | 1106202 | 6/2001 |
| EP | 1106206 | 6/2001 |
| GR | 1003262 | 11/1999 |
| WO | WO 91/06341 | 5/1991 |
| WO | WO 92/03185 | 3/1992 |
| WO | WO 95/31939 | 11/1995 |
| WO | WO 97/46244 | 12/1997 |
| WO | WO 99/13884 | 3/1999 |
| WO | WO 00/13749 | 3/2000 |
| WO | WO 01/15775 | 3/2001 |
| WO | WO 02/11648 | 2/2002 |
| WO | WO 03/017061 A2 | 2/2003 |

OTHER PUBLICATIONS

Adey, W.R., "Tissue Interactions with Nonionizing Electromagnetic Fields," *Physiological Reviews*, 1981, 61(2): 435-514.

Anninos, P.A. et al., "The Biological Effects of Magnetic Stimulation in Epileptic Patients," *Panminerva Medica*, 1999, 41(3): 207-215.

Anninos, P.A. et al., "Magnetic Stimulation in the Treatment of Partial Seizures," *Intern. J. Neuroscience*, 1991, 60: 141-175.

Beall, P.T. et al., "Distinction of Normal, Preneoplastic, and Neoplastic Mouse Mammary Primary Cell Cultures by Water Nuclear Magnetic Resonance Relaxation Times," *JNCI.*, 1980, 64(2): 335-338.

Bistolfi, F., "Biostructures and Radiation Order Disorder," *Edizioni Minerva Medica, Corso Bramante 83/85 Torino*, 1991, 61-92, 261.

Cheng, D.K., *Field and Wave Electromagnetics*, Addison Wesley Publishing Company, 1983, 255-261, 569-576.

Clegg, J.S., "Intracellular Water and the Cytomatrix: Some Methods of Study and Current Views," *The Journal of Cell Biology*, 1984, 99(1): 167-171.

Clegg, J.S., "Intracellular Water, Metabolism and Cell Architecture; Part 2," *Coherent Excitations in Biological Systems*, Herbert Frohlich Ed., Springer-Verlag, 1983, 162-177.

Clegg, J.S., "Properties and Metabolism of the Aqueous Cytoplasm and Its Boundaries," *The American Physiological Society*, 1984, R133-R151.

Cohen, D., "Magnetoencephalography: Detection of the Brain's Electrical Activity with a Superconducting Magnetometer," *Science*, 1971, 175: 664-666.

Cremer-Bartels, G., "Influence of Low Magnetic-Field-Strength Variations on the Retina and Pineal Gland of Quail and Humans," *Graefe's Archive Ophthalmology*, 1983, 220: 248-252.

Egan, T.F. et al., "Molecular Basis of Contrast in MRI," *Cell Function and Disease*, Candeo et al, (eds), Plenum Press, New York and London, 1988, 405-413.

Eichhorn, G.L., "Aging, Genetics and the Environment: Potential Errors Introduced Into Genetic Information Transfer by Metal Ions," *Mechanisms of Ageing and Developments*, 1979, 9: 291-301.

Hazlewood, C.F., "Implications of Cellular Water in Health and Disease," Second Annual Advanced Water Sciences Symposium, Dallas, TX, Oct. 4-6, 1996, 1-5.

Hazlewood, C.F., "A Role for Water in the Exclusion of Cellular Sodium—Is a Sodium Pump Needed?" *Cardiovascular Diseases, Bulletin of the Texas Heart Institute*, 1975, 2(1): 83-104.

Hazlewood, C.F., "A View of the Significance and Understanding of the Physical Properties of Cell-Associated Water," *Cell-Associated Water*, Academic Press, Inc., 1979, 165-259.

Hazlewood, C.F., "Diffusion of Water in Tissues and MRI," *Magnetic Resonance in Medicine*, 1991, 19: 214-216.

Jacobson, J.I., "Jacobson Resonance: The Coupling Mechanism for Weak Electromagnetic Field Bioeffects, and a New Way to Approach Magneto Therapy," *Panminerva Medica*, 1994, 36(1): 34-41.

Jacobson, J.I., "Exploring the Potential of Magneto-Recrystallization of Genes and Associated Structures with Respect to Nerve Regeneration and Cancer," *Int. Journal of Neuroscience*, 1992, 64(1-4): 153-165.

Jacobson, J.I., "Is the Fusion Process the Basis for Growth, Repair, and Aging?" *Panminerva Medica*, 1990, 32(3): 132-140.

Jacobson, J.I. et al., "Pico Tesla Range Magnetic Fields Tested in Four Site, Double Blind Clinical Study for Treatment of Osteoarthritic Knees," *Gazzetta Medica Italiana-Arch. Sci. Med.*, 2001, 160: 1-21.

Jacobson, J.I., "Jacobson Resonance: The Quantum-mechanical Basis for a Novel Radiological Approach to Treating Cancer and AIDS," *Frontier Perspectives*, 1996, 6(1): 17-26.

Jacobson, J.I., "Jacobson Resonance is the Basis From Which to Evaluate Potential Hazard and Therapeutic Benefit from Extrinsic Magnetic Fields," *Panminerva Medica*, 1993, 35(3): 138-148.

Jacobson, J.I. "A Look at the Possible Mechanism and Potential of Magneto Therapy," *Journal of Theoretical Biology*, 1991, 149(1): 97-119.

Jacobson, J.I., "Physics in Medicine: A Potential Unfolding in the Radiological Sciences," *Panminerva Medica*, 1996, 39(2): 111-127.

Jacobson, J.I., "Pineal-Hypothalamic Tract Mediation of Picotesla Magnetic Fields in the Treatment of Neurological Disorders," *Panminerva Medica*, 1994, 36(4): 201-205.

Jacobson, J.I., "A Theoretical Look at Gravity in the Human Cell: Its Role in Normal Cell Division as Well as Neoplasia," *Panminerva Medica*, 1992, 34(3): 96-106.

Jacobson, J.I. et al., "A Possible, Physical Mechanism in the Treatment of Neurologic Disorders with Externally Applied Pico Tesla Magnetic Fields," *Physiol. Chem. Phys. & Med. NMR*, 1994, 26: 287-297.

Kasturi, S.R., "Study of Anisotropy Nuclear Magnetic Resonance Relaxation Times of Water Protons in Skeletal Muscle," *Biophys. J.*, 1980, 30: 369-381.

Kasturi, S.R., "The Nature and Origin of Chemical Shift for Intracellular Water Nuclei in Artemia Cysts," *Biophys. J.*, 1987, 52: 249-256.

(56) References Cited

OTHER PUBLICATIONS

Kasturi, S.R., "Intracellular Water in *Artemia* Cysts (Brine Shrimp) Investigations by Deuterium and Oxygen-17 Nuclear Magnetic Resonance," *Biophys. J.*, 1990, 58: 483-491.

Lawrence, A.F. et al., "Nonlinear Wave Mechanisms in Interactions between Excitable Tissue and Electromagnetic Fields," *Neurological Research*, 1982, 4(1-2): 115-153.

Mikesell, N.D., "Structured Water: Its Healing Effects on the Diseased State," web-page at http://www.naturesalternatives.com/lc/mikesell.html as created on the internet Feb. 27, 1999.

Reuss, S., "Different Types of Magnetically Sensitive Cells in the Rat Pineal Gland," *Neuroscience Letters*, 1983, 40: 23-26.

Rorschach, H.E. et al., "Diffusion of Water in Biological Tissues," *Scanning Microscopy Supplement*, 1991, 5: S1-S9.

Sandyk, R., "Alzheimer's Disease: Improvement of Visual Memory and Visuoconstructive Performance by Treatment with PicoTesla Range Magnetic Fields," *Intern. J. Neuroscience*, 1994, 76: 185-225.

Sandyk, R., "Clinical Case Report: Magnetic Fields in the Treatment of Parkinson's Disease," *Intern. J. Neuroscience*, 1992, 63: 141-150.

Sandyk, R., "Clinical Case Report: Successful Treatment of Multiple Sclerosis with Magnetic Fields," *Intern. J. Neuroscience*, 1992, 66: 237-250.

Saxena, A. et al, "Hypothetical Mathematical Construct Explaining the Mechanism of Biological Amplification in an Experimental Model Utilizing PicoTesla (PT) Electromagnetic Fields," *Medical Hypotheses*, 2003, 60(6): 821-839.

Scherlag, B.J. et al., "The Application of Low-Level Electromagnetic Fields to the Autonomic Nerve Inputs to the Heart: Effects on Heart Rate and Atrioventricular Conduction," abstract presented at annual meeting of the American Institute of Stress, in Hawaii, 2000.

Scherlag, B.J. et al., "Magnetism and Cardiac Arrhythmias," *Cardiology in Review*, 2004, 12(2): 85-96.

Scherlag, B.J. et al., "Use of Low-Level Electromagnetic Fields and Vago-Sympathetic Stimulation to Detect and Induce the Paroxysmal Atrial Fibrillation Syndrome," abstract presented at annual meeting of the American Institute of Stress, in Hawaii, 2000.

Seitz, P.K. et al., "Proton Magnetic Resonance Studies on the Physical State of Water in *Artemia* Cysts," *The Brine Shrimp Artemia*, 1980, 2: 545-554.

Trostel, C.T., DVM, et al., "Effects of Pico-Tesla Electromagnetic Field Treatment on Wound Healing in Rats," *Am.J.Veterinary Res.*, 2003, 64(7): 845-854.

Wangsness, R.K., *Electromagnetic Fields*, John Wiley & Sons, Chapter 14, 1986, 225-236.

Welker, H.A., "Effects of an Artificial Magnetic Field on Serotonin N-Acetyltransferase Activity and Melatonin Content of the Rat Pineal Gland," *Exp. Brain. Res.*, 1983, 50: 426-432.

Yamanashi, W. et al., "The Effect of Low-Level Electromagnetic Fields on a Simple Model of Osmosis, in Vitro," abstract presented at annual meeting of the American Institute of Stress, in Hawaii, 2000.

"Jacobson Resonance Enterprises, Inc. Announces Research Findings in Breast Cancer Cells from the College of Veterinary Medicine at Mississippi State University," press release Apr. 30, 2004.

"Oklahoma University researchers report dramatic growth effects of bean sprouts using Jacobson resonation," presented to the Indian Medical Association, Calcutta, India, 2002.

Notice of Allowance and Fees Due mailed Nov. 9, 2006 for U.S. Appl. No. 10/682,131.

Office Action Summary mailed Apr. 26, 2006 for U.S. Appl. No. 10/682,131.

Office Action Summary mailed Jun. 15, 2005 for U.S. Appl. No. 10/682,131.

Office Action Summary mailed Apr. 22, 2005 for U.S. Appl. No. 10/682,131.

Amendment and Response to Office Action mailed to USPTO on Jul. 26, 2006 for U.S. Appl. No. 10/682,131.

Amendment and Response to Office Action mailed to USPTO on Dec. 15, 2005 for U.S. Appl. No. 10/682,131.

Election and Response mailed to USPTO on May 10, 2005 for U.S. Appl. No. 10/682,131.

Preliminary Amendment mailed to USPTO on Oct. 27, 2004 for U.S. Appl. No. 10/682,131.

Examiner-Initiated Interview Summary mailed Nov. 9, 2006 for U.S. Appl. No. 10/682,131.

Interview Summary mailed Aug. 1, 2006 for U.S. Appl. No. 10/682,131.

Supplementary European Search Report dated Sep. 16, 2009 for corresponding European Application No. 04809894.1.

Lu et al., "Atrial Fibrillation Begets Atrial Fibrillation Autonomic Mechanism for Atrial Electrical Remodeling Induced by Short-Term Rapid Atrial Pacing," Circ Arrhythmia Electrophysiol, Aug. 2008, pp. 184-192.

Scherlag et al., "The Autonomic Nervous System and Atrial Fibrillation: The Roles of Pulmonary Vein Isolation and Ganglionated Plexi Ablation," Journal of Atrial Fibrillation, Aug. 2009, vol. 1, Issue 8, pp. 1-16.

Qin, C. et al., "Effects on Rats of Low Intensity and Frequency Electromagnetic Field Stimulation on Thoracic Spinal Neurons Receiving Noxious Cardiac and Esophageal Inputs," *Neuromodulation*, 8(2): 79-87, 2005.

Office Action dated Aug. 5, 2009 for corresponding Canadian Patent Application No. 2,542,119 filed Oct. 8, 2004.

Office Action mailed May 17, 2010 corresponding to EP Patent Application No. 04 809 894-1.

Presentation at the American College of Cardiology (ACC), "Magnetic Therapy and the Autonomic Nervous Sytem," 2004.

United States Patent and Trademark Office, Office Action, U.S. Appl. No. 13/031,369, mailed Aug. 9, 2012.

European Patent Office, Communication Pursuant to Article 94(3) EPC, Application No. 04809894, dated Jul. 25, 2012.

Canadian Patent Office, Office Action, Application No. 2,542,119 mailed Feb. 14, 2012.

United States Patent and Trademark Office, Office Action, U.S. Appl. No. 13/031,369 mailed Jan. 28, 2013.

European Patent Office, Communication Pursuant to Article 94(3) EPC, Application No. 04 809 894.1-1652 mailed Aug. 12, 2013.

\* cited by examiner

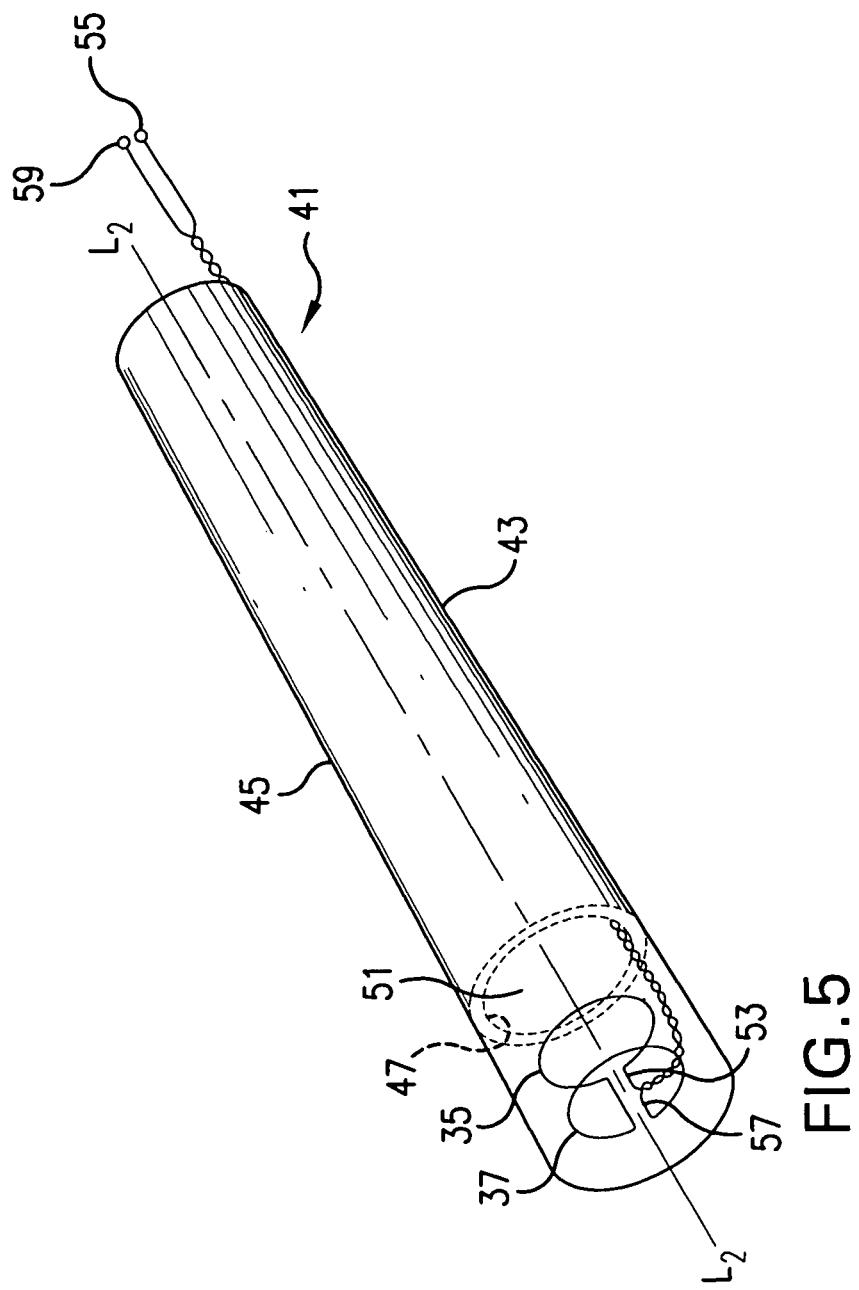

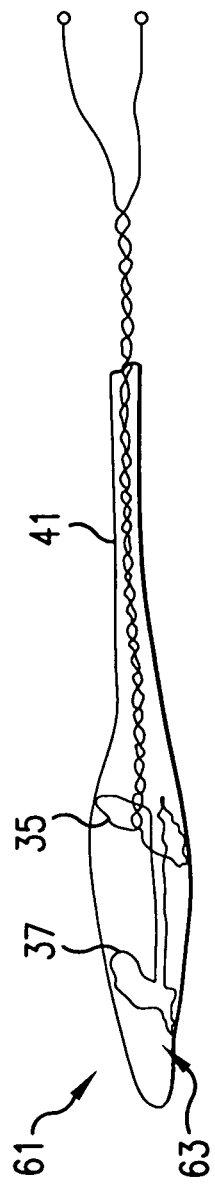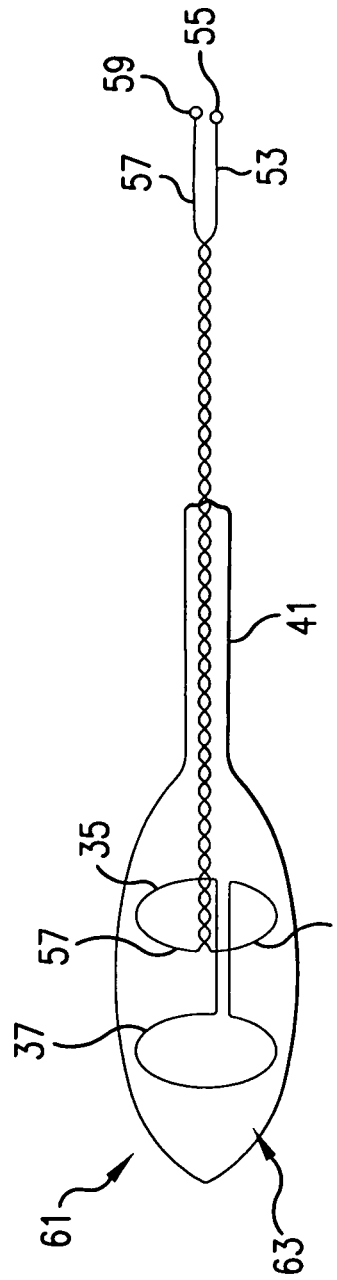
FIG.6A
FIG.6B

CARDIOELECTROMAGNETIC TREATMENT

PRIORITY CLAIM TO RELATED APPLICATIONS

This application is a divisional application of U.S. patent application Ser. No. 10/682,131, filed Oct. 9, 2003, now U.S. Pat. No. 7,186,209.

BACKGROUND OF THE INVENTION

1. Field of the Invention

This invention generally relates to cardiology and, more particularly, to non-invasive and invasive cardio-electromagnetic therapy.

2. Description of the Background

Intrinsic rhythmicity is a well-established cardiac property. Intrinsic rhythmicity is the heart's ability to initiate its own heart rate, rhythm, and conductivity without nervous innervation. Even though the heart can initiate its own heart rate, rhythm, and conductivity, the autonomic nervous system is known to strongly influence heart rate, rhythm, and conductivity. The autonomic nervous system, in fact, has a great influence on other cardiac properties such as contractility (e.g., heart pump strength) and refractoriness (e.g., excitable readiness).

The autonomic nervous system has two components. One component, the parasympathetic nervous system, can cause slowing of the heart rate and slowing of atrio-ventricular (A-V) conduction in the heart. The A-V conduction rate is slowed when the parasympathetic nervous system releases acetylcholine at the atrio-ventricular node. The heart rate is slowed when the parasympathetic nervous system releases acetylcholine at the nerve terminals at the sino-atrial node. The sino-atrial node is considered the heart's primary "pacemaker."

The other component of the autonomic nervous system is the sympathetic nervous system. The sympathetic nervous system, conversely, causes speeding of the heart rate, speeding of the A-V conduction rate, and constriction of blood vessels. The sympathetic nervous system releases neurotransmitters, such as epinephrine and norepinephrine, to speed heart rate and A-V conduction. The sympathetic nervous system is also known to cause an increase in the force of contraction of the heart muscle. The neurotransmitters epinephrine and norepinephrine have also been implicated in the irregular heart rhythm called arrhythmias. Arhythmias are irregularities of the heart rate arising from either the atria or the ventricles.

Because the autonomic nervous system is known to influence heart properties, research has focused on stimulating the autonomic nervous system. One research avenue shows that electrical stimulation of the autonomic nervous system causes the release of neurotransmitters. These neurotransmitters, as mentioned above, affect heart rate, rhythm, conductivity, and contractility. This electrical stimulation has, however, always required surgical dissection of the parasympathetic and sympathetic nerves. Surgical dissection of nerve tissue is not acceptable or practical for clinical studies and clinical purposes.

Another research avenue has been chemical stimulation. Researchers have chemically synthesized the neurotransmitters that affect heart rate, rhythm, conductivity, and contractility. This chemical stimulation has proven useful in modulating cardiac properties in clinical circumstances. "Beta-blockers" such as propanolol, for example, have been used as sympathetic nerve blocking agents. These beta-blockers have proven invaluable in controlling abnormalities of the heart's rhythm, rate, and conduction.

Chemical stimulation, however, is approached with caution. The effects of chemical stimulation are not completely understood. Chemically synthesized neurotransmitters, or similar agents, are very technologically new and the long-term effects are unknown. A further problem is that patients are often found to become non-compliant, i.e., they stop their medication or their compliance is irregular.

Accordingly, there is a need to stimulate the autonomic nervous system that does not require surgical dissection of nerve tissue, which is acceptable to clinical subjects, and is cost effective to administer. These advantages and other advantages are provided by the system and method described herein, and numerous disadvantages of existing techniques are avoided.

SUMMARY OF THE INVENTION

In accordance with one aspect of the invention, there is provided a method of treatment or prophylaxis of a disease state or a condition. An organism is subjected to electromagnetic field having an electromagnetic flux density from about $5 \times 10^{-6}$ gauss to about $1 \times 10^{-12}$ gauss and a frequency of between about zero and about 140 Hertz. The electromagnetic field is applied therapeutically to treat or prevent cardiac diseases and conditions. The diseased state or condition may include elevated heart rate, irregular heart rate, elevated blood pressure, cardiovascular failure, blood clots, atrial fibrillation, ventricular fibrillation, atrioventicular blockage, diseased heart valves, enlarged heart, circulatory blockage, coronary insufficiencies, and ischemia.

In a more specific aspect, the magnetic flux density of the field is calculated using the formula $mc^2 = Bvlq$, where B is the magnetic flux density, m is the mass of one or more targets, c is the speed of light, v is the inertial velocity of the mass, l is the length of the organism to which the field will be applied, and q is a unity of charge.

Preferably, the electromagnetic field is administered to affect the autonomic nervous system. In one aspect, the electromagnetic field is administered in a range between about 2 to about $3.4 \times 10^{-8}$ gauss and a frequency between about 0 to about 28 Hertz to affect the parasympathetic nervous system. In an alternative aspect, the electromagnetic field is administered in a range between about $7.6 \times 10^{-8}$ to about $1 \times 10^{-6}$ gauss at a frequency from about 0 to about 28 Hertz to affect the sympathetic nervous system.

The organism may be subjected to the electromagnetic field by either placing the organism inside an external apparatus for generating the electromagnetic field. Alternatively, the organism may be subjected to the electromagnetic field by implanting a device for generating the electromagnetic field directly into the organism. The device is implanted in proximity to the organ to which treatment is targeted. Thus, the treatment may be administered either non-invasively or invasively.

In another aspect of the invention, a device invasively administers an electromagnetic field in an organism. The device has at least one inductor for emitting electromagnetic energy, which has a magnetic flux density from about $5 \times 10^{-6}$ gauss to about $1 \times 10^{-12}$ gauss and a frequency between 0 and 140 Hertz. The device also has a means for implanting the inductor into the organism. The inductor may be either a Helmholtz coil, a solenoid coil, or a saddle coil. The means for implanting may be a catheter or a stent. One of ordinary skill in the art would understand that other means for implanting the inductor are possible and easily interchanged with a catheter or stent, for example, any medical device having a receptacle for the inductor such that the inductor may be implanted into an organism.

In a more specific aspect, the device has a first wire and a second wire connected to the ends of the inductor, and a signal generator for generating an electric signal through the first and second wires and an attenuator for attenuating the signal. The attenuator and the signal generator may not be implanted into the organism.

In another more specific aspect, the device has a balloon attached to the first end of the catheter tube, which is inflatable and deflatable in response to fluid pressure within the catheter tube. The inductor is located within the balloon. Preferably, the inductor expands and contracts correspondingly with the balloon inflation and deflation.

In yet another aspect, a device invasively administers an electromagnetic field in an organism. The device has at least one solenoid for emitting the electromagnetic field, which has a magnetic flux density from about $5\times10^{-6}$ gauss to about $1\times10^{-12}$ gauss and a frequency between about 0 and about 140 Hertz. A capacitor is operatively connected to the solenoid. The device also has a means for implanting the solenoid and the capacitor into the organism, and a means for inducing an electric current in the solenoid. The means for implanting may be a stent. One of ordinary skill in the art would understand that other means for implanting the inductor are possible and easily interchanged with a stent, for example, a catheter or other medical device having a receptacle for the inductor.

In a more specific aspect, the means for inducing the electric current in the solenoid is a catheter that is removably insertable into the solenoid. A second solenoid coil is attached to the catheter, which is also removeably insertable into the solenoid. A means for generating an electric current through the second solenoid coil is provided. The electric current in the second solenoid induces an electric current in the first solenoid coil. Preferably the means for inducing the electric current is a first wire attached to a first end of the second solenoid coil; a second wire attached to a second end of the second solenoid coil, an attenuator operatively connected to the first and second wires, and a signal generator operatively connected to the first and second wires. The signal generator generates a signal, which is attenuated by the attenuator and carried along the first and second wires. The signal generator and the attenuator are not implanted in the organism.

In an alternative aspect, the means for inducing the electric current in the solenoid is an electromagnetic field generator that is external to the organism. In one specific aspect, the electromagnetic field generator may be a Helmholtz coil external to the organism. The organism in which the solenoid has been implanted is placed inside of the Helmholtz coil such that a current is induced in the solenoid coil. An attenuator is connected to the Helmholtz coil and a signal generator is connected to the attenuator for generating a signal to the Helmholtz coil. In an alternative specific aspect, the electromagnetic field generator is a second solenoid external to the organism. The organism in which the first solenoid has been implanted is placed inside of the second solenoid such that a current is induced in the first solenoid coil. An attenuator is operatively connected to the second solenoid coil and a signal generator is operatively connected to the attenuator for generating a signal to the second solenoid coil.

BRIEF DESCRIPTION OF THE DRAWINGS

These and other features, aspects, and advantages of the present invention will be better understood when the following Detailed Description is read with reference to the accompanying drawings.

FIG. 5 is an isometric view of a catheter for invasively administering the very low frequency electromagnetic treatment.

FIG. 6 includes two partial views of an alternative embodiment of the catheter shown in FIG. 5.

DETAILED DESCRIPTION

Figure 1:
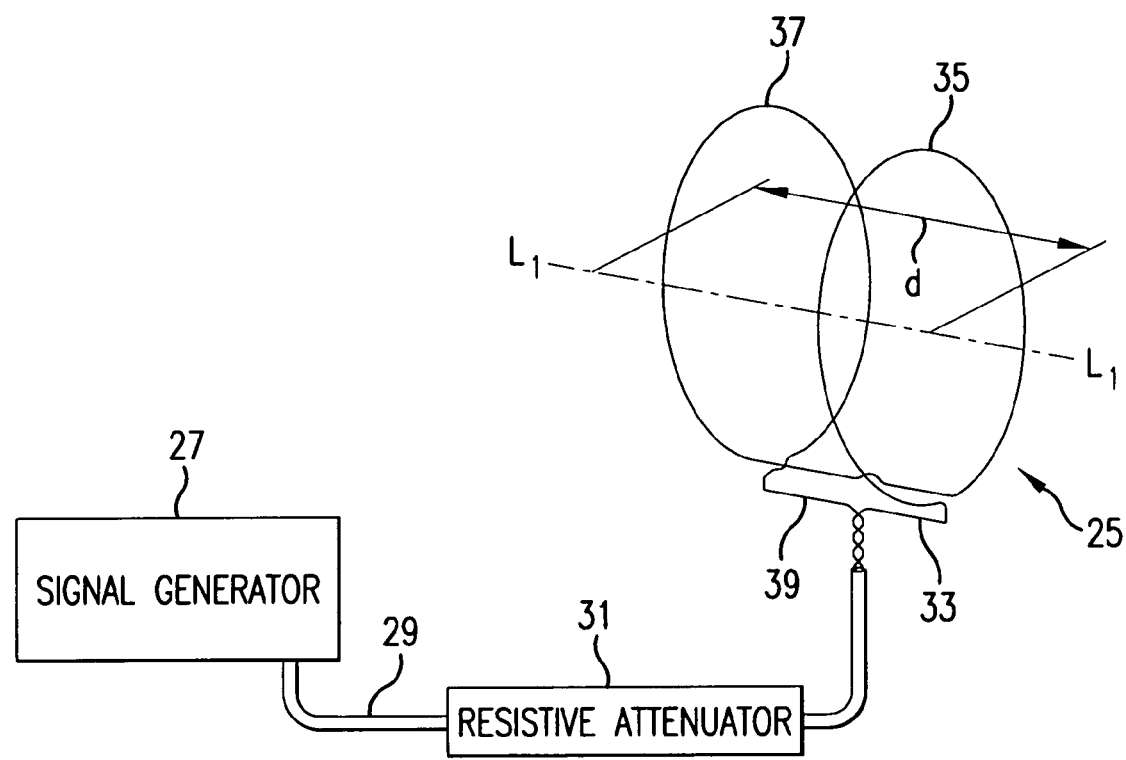
FIG. 1 shows a system used to treat persons or mammals, with extremely low frequency electromagnetic fields.

FIG. 1 shows a system 25 used to treat persons or other organisms, with extremely low frequency electromagnetic fields. By "low frequency electromagnetic fields" is meant a frequency of 0 to 140 Hz. A signal generator 27 generates an input signal, typically of a voltage ranging from about $10^{-3}$ to about $10^{-12}$ volts, or a current of about $10^{-5}$ to about $10^{-12}$ amperes having an Electric Field strength of about $10^{-3}$ volts per centimeter to about $10^{-12}$ volts per centimeter. The input signal transmitted along a first wire 29 and is received by a voltage attenuator 31. The voltage attenuator 31 attenuates the signal. The attenuated signal is transmitted along a second wire 33 and is received by at least one inductor. By the term inductor is meant an electronic component that stores energy in the form of a magnetic field. An inductor may be a wire loop or coil in a given shape to approximate unidirectional current by inertial—electromagnetic induction. The inductor could also be a magnet. The inductor may or may not include a dielectric material. As would be understood by one of ordinary skill in the art, the relationship between the magnetic flux ("B"), the magnetic constant of the dielectric ($\mu_o$) and the magnetic field strength (H) is an example of an inductor is shown in FIG. 1 as a first coil 35 arranged in series with a second coil 37. The attenuated signal, after flowing through the inductor, returns to the signal generator 27 along a third wire 39 to complete a circuit.

As would be understood by one of ordinary skill in the art, current flowing through a wire is widely known to produce magnetic flux density. See DAVID K. CHENG, FIELD AND WAVE ELECTROMAGNETICS 225-50 (1983). Thus, many types of wire arrangements produce a magnetic flux density and can be substituted for the first and second coils 35 and 37 shown in FIG. 1. The first and second coils 35 and 37 are in an exemplary form, a Helmholtz coil. A Helmholtz coil is a pair of flat coils having equal numbers of turns and equal diameters arranged with a common axis and connected in series such that the electrical current flows in the same direction around both coils such that a magnetic field is produced. Thus, the first and second coils 35 and 37 depicted in FIG. 1 may have several turns of wire. A Helmholtz coil produces a more uniform magnetic field than a single coil. Examples of other wire arrangements capable of producing magnetic fields include solenoid coils, saddle coils, toroidal, and poloidal coils. Solenoid coils are a wound coil arrangement of wire carrying an electric current for producing a magnetic field. A saddle coil is a pair of coils having equal numbers of turns and equal diameters arranged with a common axis and connected in series such that the electrical current flows in opposite directions around both coils such that a magnetic field is produced. As would be understood by one of ordinary skill in the art, the "coil" of wire is not necessarily circular in shape. For example, a solenoidal-like coil may be constructed such that turns of coil at some points along the coil are closer together than at other points in the coil. In addition, the coils may be in any shape, such as rectangles, squares, and ovals, so long as a magnetic field is produced by current flowing through the wires. Furthermore, the electric current carried by the wire may be either a direct current (DC) or a time-varying current, called an alternating current (AC). An alternating current may take any wave form, for example, sinusoidal, rectilinear, triangular and trapezoidal. Various waveforms may also be interchangeable.

The system 25 can be used to subject patients to the magnetic flux density. If a steady, static current, or a time-varying current, flows through a wire, such as the first and second coils 35 and 37, experiments have shown the electromagnetic field has biological parasympathetic and sympathetic effects. The system 25 can, therefore, be used to implement a method of treatment or prophylaxis of a disease state or a condition ameliorated or prevented by electromagnetic radiation. The method includes subjecting an organism to electromagnetic radiation having a magnetic flux density from about $5 \times 10^{-6}$ gauss and about $1 \times 10^{-12}$ gauss and a frequency between about zero and about 140 Hertz. The method, more particularly, is applied at very low frequencies in the range of about zero to about twenty eight Hertz (28 Hz).

The method can be used to ameliorate or prevent many common ailments. The diseased state or condition may include elevated heart rate, irregular heart rate, elevated blood pressure, cardiovascular failure, cancer, cataracts, immunological conditions (such as HIV/AIDS), blood clots, atrial fibrillation, ventricular fibrillation, and atrioventicular blockage. The diseased state or condition may also include diseased heart valves, enlarged heart, circulatory blockage, coronary insufficiencies, and ischemia.

Experiments have shown that electromagnetic fields in the range of about one to about one hundred picoTesla (100 pT) (Or between about $10^{-8}$ gauss to about $10^{-6}$ gauss) produces either parasympathetic or sympathetic effects. These parasympathetic and sympathetic effects occur when electromagnetic fields are impinged upon biosystems. Specifically, parasympathetic effects are observed when the electromagnetic field is administered in a range between about $10^{-12}$ gauss to about $3.4 \times 10^{-8}$ gauss. Or, the electromagnetic field may be administered in a range between about $2 \times 10^{-8}$ gauss to about $3.8 \times 10^{-8}$ gauss. Or, the electromagnetic field may be administered in a range between about $2.8 \times 10^{-8}$ gauss to about $3.4 \times 10^{-8}$ gauss. Sympathetic effects are observed when the electromagnetic radiation is administered in a range between about $7.5 \times 10^{-8}$ to about $1 \times 10^{-6}$ gauss.

By comparison, much larger electromagnetic fields are present in the environment from a variety of sources. The geomagnetic field is about 0.5 gauss, which is millions of times stronger than the electromagnetic fields used in the system and method described herein. Electromagnetic fields are commonly used in a medical imaging technique called magnetic resonance imaging (MRI) to image internal structures. Typical MRI fields are about 10,000 gauss. Electromagnetic fields produced by power lines and household appliances are more than 100,000 times stronger than the fields used in the system and method described herein.

It is believed that these sympathetic and parasympathetic effects from weak or low electromagnetic fields (less than about $10^{-6}$ gauss, preferably about $10^{-8}$ gauss to about $10^{-6}$ gauss are based upon cellular resonances with particular masses associated with particular cellular dimensions and the cyclotron resonance associated with lower frequencies of electromagnetic fields. Thus, specific electromagnetic flux densities administered at specific frequencies stimulate ganglia on the heart that regulate, as part of the autonomic nervous system, the heart rate and electrical conduction in the heart. It is believed that the relation of subatomic particles to the distances a cell border covers in space-time regulate the structural and functional interactions of living matter. Thus, the relationship between subatomic particles and the distances the cell border covers determine the appropriate electromagnetic flux density and frequency for regulation of structural and functional interactions in a living system. See U.S. Pat. No. 5,269,746 to Dr. Jerry I. Jacobson, issued Dec. 14, 1993. The Jacobson equation is:

$$mc^2 = Blvq,$$

where
m=mass of a particle in a "box" or a "string;"
B=the magnetic flux density;
q=a unit charge of one abcoulomb in the CGS unit system;
v=velocity of the carrier or "string" in which the particle exists, for example, the orbital or rotational velocity of the earth; and
l=length of the carrier or "string."

Specifically, the particle in the carrier (also referred to herein as a "box" or "string") may be a particle such as an electron, photon, or proton in a cell (carrier) or a molecule (particle) in a biological system (carrier). More specifically, the molecule may be any molecule critical to a biological system. Thus, if the carrier is an organism such as a dog or a human, the length of the carrier is the height of the organism. Harmonic resonances may be added by using the cell (or organelle) of the organism as the carrier, and a subatomic particle as the target particle.

Table 1 shows the magnetic flux density calculated for electrons and protons inside a cell. Thus, the length of the box is the diameter of the cell. The magnetic flux densities calculated in Table 1 (0.028-0.034 µG) are typical for subatomic particles in a cell.

TABLE I

| Mass | Inertial Velocity (v) | Length of box (l) | Magnetic Profile (B) flux density |
|---|---|---|---|
| (E) electron | earth rotational (ER) ($4.6 \times 10^4$ cm/s) | 5.3 microns | .034 µG |
| $e^-$ | ER | 6.37 microns | .028 µG |
| $p^+$ | star cluster (SC) ($3.2 \times 10^7$ cm/s) | $1.36 \times 10^{-3}$ cm | .034 µG |

Table 2 shows the calculation of the magnetic flux using the Jacobson equation for various molecules critical to biological systems. The resulting magnetic flux densities in living systems using critical molecules are similar to the magnetic flux densities for subatomic particles in a cell calculated in Table 1. Namely, these values are between about 0.028 µG and about 0.037 µG.

TABLE II

| Mass | Inertial Velocity (v) | Length of box (l) | Magnetic Profile (B) |
|---|---|---|---|
| 3,325.8 Daltons VIP-D-Phe-2 vasointestinal peptide | solar system $1.92 \times 10^6$ cm/s (SS) | (dog) 70 cm | .037 μG |
| VIP lys-1-pro-2,5 vasointestinal peptide | SS | (dog) 76 cm | .037 μG |
| | earth orbital (EO) $3 \times 10^6$ cm/s | dog 54 cm | .032 μG |
| epinephrine 184 daltons | EO | dog 56 cm | .031 μG |
| | earth rotational (ER) $4.6 \times 10^4$ cm/s | human $1.7 \times 10^2$ cm | .0347 μG |
| serotonin (176 Da) | ER | human | .032 μG |
| Acetylcholine | ER | human | .0334 μG |
| Tubulin Subunits adenosine | SC | human | 03 μG |
| | EO | rat (22 cm) | .0346 μG |

The particles in this study are important, critical molecules and other particles selected based on their relationship to particular conditions. More specifically, the particles play a role in nerve repair, growth, and regeneration. Some examples of these important biological particles include nerve growth factor (NGF), homeoboxes, neurotransmitters, cytokines, motor proteins, and structural proteins. Some other examples include kinesine, microtubule associated protein (MAP), spectrin, brain specific fodrin, neurofilaments, tubulin, and platelet-derived growth factor (PDGF).

A critical molecule is selected, and the appropriate magnetic flux density is calculated. The frequency may also be calculated using the ion cyclotron resonance equation $$f = 10 \times \frac{qB}{2\pi m}$$

to determine the frequency of the externally-applied magnetic flux. Because the intensity B of the magnetic flux density was previously calculated using the Jacobson equation, the ion cyclotron resonance equation can be used to determine the frequency of the externally-applied magnetic flux. See U.S. Pat. No. 5,269,746 to Dr. Jerry I. Jacobson, issued Dec. 14, 1993.

It has been found that the heart rate, for example, can be slowed using a magnetic field in the range of about two (2) to about 3.4 picoTesla. The parasympathetic effects seem to be a consequence of stimulating ganglia on the heart which autonomically regulate electrical conduction in the heart. Higher ranges of magnetic fields, from about zero to about one hundred picoTesla (100 pT), have, conversely, sympathetic effects. It is believed that parasympathetic and sympathetic effects are observed because inter-atomic relations as expressed in the Jacobson and the ion cyclotron resonance equations, regulate structural and functional interactions in all matter.

The following table may be used to determine the appropriate magnetic field and frequency to treat any condition dependent upon critical molecules of specific molecular weights. The appropriate magnetic field and frequency is determined using the Jacobson equation and the ion cyclotron resonance equation, respectively, by selecting a target molecule or particle relevant to the condition and selecting the magnetic field corresponding to the target molecule's mass. The magnetic field (B) is calculated either in accordance with the earth's orbital velocity, the earth's rotational velocity, or the star cluster velocity which the earth is in which circles the center of the Milky Way Galaxy (v). The velocity of the system corresponds to a harmonic resonance for the particular system. The (L) length used is 5'8" average human length. As would be understood by one of ordinary skill in the art, examples of critically important molecules relevant to cardiac patients include nerve growth factor (NGF), homeoboxes, neurotransmitters, cytokines, motor proteins, structural proteins, kinesine, microtubule associated protein (MAP), spectrin, brain specific fodrin, neurofilaments, tubulin, platelet derived growth factor (PDGF), and other biological molecules related to cardiac function. The mass of these critical or target particles is well known.

TABLE 3

Table For Humans
(Length = $1.7 \times 10^2$ cm)

| Inertial Velocities: | $3.22 \times 10^7$ cm/s | star cluster (SC) |
|---|---|---|
| | $2.98 \times 10^6$ cm/s | earth orbital (EO) |
| | $4.642 \times 10^4$ cm/s | rotational earth (ER) |

Note: 1 dalton is an atomic mass unit (a.m.u.) symbol: μ, which is conventionally assigned a value equal to one twelfth of an atom of the mass of the most abundant isotope of carbon, carbon 12. Therefore, carbon twelve is assigned an atomic mass unit, or dalton, of 12.

| B (microgauss) FIELD | (Hertz) FREQUENCY | target masses in (daltons) EO | target masses in (daltons) SC |
|---|---|---|---|
| 0.001 | 0.028000001 | 339.321 | 3619.424 |
| 0.002 | 0.055000001 | 678.642 | 7238.848 |
| 0.003 | 0.084000002 | 1017.963 | 10858.272 |
| 0.004 | 0.112000002 | 1357.284 | 14477.696 |
| 0.005 | 0.140000030 | 1696.605 | 18067.120 |
| 0.006 | 0.168000003 | 2036.926 | 21716.544 |
| 0.007 | 0.196000004 | 2375.247 | 25335.968 |
| 0.008 | 0.224000004 | 2714.568 | 28955.392 |
| 0.009 | 0.252000005 | 3053.889 | 32574.816 |
| 0.010 | 0.280000006 | 3393.210 | 36194.240 |
| 0.011 | 0.308000006 | 3732.531 | 39813.664 |
| 0.012 | 0.336000007 | 4071.852 | 43433.088 |
| 0.013 | 0.640000070 | 4411.173 | 47052.512 |
| 0.014 | 0.392000008 | 4750.494 | 50871.936 |
| 0.015 | 0.420000008 | 5089.815 | 54291.360 |
| 0.016 | 0.448000009 | 5429.136 | 57910.784 |
| 0.017 | 0.478000010 | 5768.457 | 61530.208 |
| 0.018 | 0.504000010 | 6107.778 | 65149.632 |
| 0.019 | 0.532000011 | 6447.099 | 68769.058 |
| 0.020 | 0.560000011 | 6786.420 | 72388.480 |
| 0.021 | 0.588000012 | 7125.741 | 76007.904 |
| 0.022 | 0.618000012 | 7465.062 | 79627.328 |
| 0.023 | 0.644000013 | 7804.383 | 83246.752 |
| 0.024 | 0.372000013 | 8143.704 | 86866.176 |
| 0.025 | 0.700000014 | 8483.025 | 90485.600 |
| 0.026 | 0.728000015 | 8822.346 | 94105.240 |
| 0.027 | 0.756000015 | 9161.667 | 97724.448 |
| 0.028 | 0.784 | 9500.988 | 101343.872 |
| 0.029 | 0.812000016 | 9840.309 | 107963.296 |
| 0.030 | 0.840000017 | 10179.630 | 108582.720 |
| 0.031 | 0.868000017 | 10518.951 | 112202.144 |
| 0.032 | 0.896000018 | 10856.272 | 115821.568 |
| 0.033 | 0.924000018 | 11197.593 | 119440.992 |
| 0.034 | 0.952000019 | 11536.914 | 123060.416 |
| 0.035 | 0.980000020 | 11876.235 | 126679.840 |
| 0.036 | 1.008000020 | 12215.656 | 130299.264 |
| 0.037 | 1.036000021 | 12554.877 | 133918.888 |
| 0.038 | 1.064000021 | 12894.198 | 137538.112 |
| 0.039 | 1.092000022 | 13233.519 | 141157.538 |
| 0.040 | 1.120000022 | 13572.840 | 144776.960 |
| 0.041 | 1.148000023 | 13912.161 | 148396.384 |
| 0.042 | 1.176000024 | 14251.482 | 152015.808 |
| 0.043 | 1.204000024 | 15690.803 | 155835.232 |
| 0.044 | 1.232000025 | 14930.124 | 159254.658 |
| 0.045 | 1.260000025 | 15269.445 | 162874.080 |
| 0.046 | 1.288000026 | 15608.766 | 166493.504 |
| 0.047 | 1.316000026 | 15978.087 | 170112.928 |

TABLE 3-continued

| | | | |
|---|---|---|---|
| 0.048 | 1.344000027 | 16287.408 | 173732.352 |
| 0.049 | 1.372000027 | 16626.729 | 177351.776 |
| 0.050 | 1.400000028 | 16966.050 | 180971.200 |
| 0.051 | 1.428000029 | 17305.371 | 184590.624 |
| 0.052 | 1.456000029 | 17644.692 | 188210.048 |
| 0.053 | 1.484000030 | 17984.013 | 191829.472 |
| 0.054 | 1.512000030 | 18323.334 | 196448.896 |
| 0.055 | 1.640000031 | 18662.655 | 199068.320 |
| 0.056 | 1.568000031 | 19001.976 | 202687.744 |
| 0.057 | 1.596000032 | 19341.297 | 206307.168 |
| 0.058 | 1.624000032 | 19680.618 | 209926.592 |
| 0.059 | 1.652000033 | 20019.939 | 213546.016 |
| 0.060 | 1.680000033 | 20359.260 | 217165.440 |
| 0.061 | 1.708000034 | 20696.581 | 220784.864 |
| 0.062 | 1.736000035 | 21037.902 | 224404.288 |
| 0.063 | 1.764000035 | 21377.223 | 228023.712 |
| 0.064 | 1.792000036 | 21716.544 | 231643.163 |
| 0.065 | 1.820000036 | 22066.866 | 235262.560 |
| 0.066 | 1.848000037 | 22395.186 | 238881.984 |
| 0.067 | 1.876000038 | 22734.507 | 242501.408 |
| 0.068 | 1.904000038 | 23073.828 | 246120.832 |
| 0.069 | 1.932000039 | 23413.149 | 249740.256 |
| 0.070 | 1.960000039 | 23752.470 | 253359.680 |
| 0.071 | 1.988000040 | 24091.791 | 256979.104 |
| 0.072 | 2.016000040 | 24431.112 | 260598.528 |
| 0.073 | 2.044000041 | 24770.433 | 264217.952 |
| 0.074 | 2.072000041 | 25109.754 | 267837.376 |
| 0.075 | 2.100000042 | 25449.075 | 271456.800 |
| 0.076 | 2.128000043 | 25788.396 | 275076.224 |
| 0.077 | 2.156000043 | 26127.717 | 278695.648 |
| 0.078 | 2.184000044 | 26467.038 | 282315.072 |
| 0.079 | 2.212000044 | 26806.359 | 285934.496 |
| 0.080 | 2.240000045 | 27145.680 | 289553.920 |
| 0.081 | 2.268000045 | 27485.001 | 293173.344 |
| 0.082 | 2.296000046 | 27824.322 | 296792.768 |
| 0.083 | 2.324000046 | 28163.643 | 300412.192 |
| 0.084 | 2.352000047 | 28502.964 | 304031.616 |
| 0.085 | 2.380000028 | 28842.285 | 307651.040 |
| 0.086 | 2.408000048 | 29181.606 | 311270.464 |
| 0.087 | 2.436000049 | 29520.927 | 314889.888 |
| 0.088 | 2.464000049 | 29860.248 | 318509.312 |
| 0.089 | 2.492000050 | 30199.569 | 322128.736 |
| 0.090 | 2.520000050 | 30538.890 | 325748.160 |
| 0.091 | 2.548000051 | 30878.211 | 329367.584 |
| 0.092 | 2.576000052 | 31217.532 | 332987.008 |
| 0.093 | 2.604000052 | 31556.853 | 336606.432 |
| 0.094 | 2.632000053 | 31896.174 | 340225.856 |
| 0.095 | 2.660000053 | 32235.495 | 343845.280 |
| 0.096 | 2.688000054 | 32874.816 | 347464.704 |
| 0.097 | 2.716000054 | 32914.137 | 351084.128 |
| 0.098 | 2.744000055 | 33253.458 | 354703.552 |
| 0.099 | 2.722000055 | 33592.779 | 358322.976 |
| 0.100 | 2.800000056 | 33932.100 | 361942.400 |
| 0.101 | 2.828000057 | 34271.421 | 365561.824 |
| 0.102 | 2.856000057 | 34610.742 | 369181.248 |
| 0.103 | 2.884000058 | 34950.063 | 372800.672 |
| 0.104 | 2.912000058 | 35289.384 | 376420.096 |
| 0.105 | 2.940000059 | 35628.705 | 380039.520 |
| 0.106 | 2.968000059 | 35968.026 | 383658.944 |
| 0.107 | 2.996000060 | 36307.347 | 387278.368 |
| 0.108 | 3.024000060 | 38646.668 | 390897.792 |
| 0.109 | 3.052000061 | 36985.989 | 394517.216 |
| 0.110 | 3.080000062 | 37325.31 | 398136.640 |
| 0.111 | 3.108000062 | 37664.631 | 401756.064 |
| 0.112 | 3.136000063 | 38003.952 | 405375.488 |
| 0.113 | 3.164000083 | 38343.273 | 408994.912 |
| 0.114 | 3.192000064 | 38682.594 | 412614.336 |
| 0.115 | 3.220000064 | 39021.915 | 416233.760 |
| 0.116 | 3.248000065 | 39361.236 | 419853.184 |
| 0.117 | 3.276000066 | 39700.557 | 423472.608 |
| 0.118 | 3.304000066 | 40039.878 | 427092.032 |
| 0.119 | 3.332000067 | 40379.199 | 430711.456 |
| 0.120 | 3.360000067 | 40718.520 | 434330.880 |
| 0.121 | 3.388000068 | 41057.841 | 437950.304 |
| 0.122 | 3.416000068 | 41397.162 | 441589.728 |
| 0.123 | 3.444000069 | 41736.483 | 445189.152 |
| 0.124 | 3.472000069 | 42075.804 | 448808.576 |
| 0.125 | 3.500000070 | 42415.125 | 452428.000 |
| 0.126 | 3.528000071 | 42754.446 | 456047.424 |
| 0.127 | 3.556000071 | 43093.767 | 459666.848 |
| 0.128 | 3.584000072 | 43433.088 | 463286.272 |
| 0.129 | 3.612000072 | 43772.409 | 466905.696 |
| 0.130 | 3.640000073 | 44111.730 | 470525.100 |
| 0.131 | 3.668000073 | 44451.051 | 474144.544 |
| 0.132 | 3.696000074 | 44790.372 | 477763.968 |
| 0.133 | 3.724000074 | 45129.693 | 481383.392 |
| 0.134 | 3.752000076 | 45469.014 | 485002.816 |
| 0.135 | 3.780000076 | 45808.335 | 488622.240 |
| 0.136 | 3.808000076 | 46147.658 | 492241.664 |
| 0.137 | 3.936000077 | 46486.977 | 495861.088 |
| 0.138 | 3.864000077 | 46826.298 | 499480.512 |
| 0.139 | 3.892000078 | 47165.619 | 503099.936 |
| 0.140 | 3.920000078 | 47504.940 | 506719.360 |
| 0.141 | 3.948000079 | 47844.261 | 510338.784 |
| 0.142 | 3.976000080 | 48183.582 | 513958.208 |
| 0.143 | 4.004000080 | 48522.903 | 517577.632 |
| 0.144 | 4.032000081 | 48862.224 | 521197.056 |
| 0.145 | 4.060000810 | 49201.545 | 524816.480 |
| 0.146 | 4.088000082 | 49540.866 | 528435.904 |
| 0.147 | 4.116000082 | 49880.187 | 532055.328 |
| 0.148 | 4.144000083 | 50219.508 | 535674.752 |
| 0.149 | 4.172000083 | 50558.829 | 539294.176 |
| 0.150 | 4.200000084 | 50898.150 | 542913.600 |
| 0.151 | 4.228000085 | 51237.471 | 546733.024 |
| 0.152 | 4.258000085 | 51576.792 | 550152.448 |
| 0.153 | 4.284000086 | 51916.113 | 553771.872 |
| 0.154 | 4.312000086 | 52255.434 | 557391.296 |
| 0.155 | 4.340000087 | 52594.755 | 561010.720 |
| 0.156 | 4.368000087 | 52934.076 | 564630.144 |
| 0.157 | 4.396000088 | 53273.397 | 568249.568 |
| 0.158 | 4.424000088 | 53812.718 | 571868.992 |
| 0.159 | 4.452000089 | 53952.039 | 575488.416 |
| 0.160 | 4.480000090 | 54291.360 | 579107.840 |
| 0.161 | 4.508000090 | 54630.681 | 582727.264 |
| 0.162 | 4.536000091 | 54970.002 | 586346.688 |
| 0.163 | 4.564000091 | 55309.323 | 589966.112 |
| 0.164 | 4.592000092 | 55648.644 | 593585.536 |
| 0.165 | 4.620000092 | 55987.965 | 597204.960 |
| 0.166 | 4.648000093 | 56327.286 | 600824.384 |
| 0.167 | 4.676000094 | 56686.607 | 604443.808 |
| 0.168 | 4.704000094 | 57005.928 | 608063.232 |
| 0.169 | 4.732000095 | 57345.249 | 611682.858 |
| 0.170 | 4.760000095 | 57684.570 | 615302.080 |
| 0.171 | 4.788000096 | 58023.891 | 618921.504 |
| 0.172 | 4.816000096 | 58363.212 | 622540.928 |
| 0.173 | 4.844000097 | 58702.533 | 628160.352 |
| 0.174 | 4.872000097 | 59041.854 | 629779.776 |
| 0.175 | 4.900000098 | 59381.175 | 633399.200 |
| 0.176 | 4.928000099 | 59720.496 | 637018.624 |
| 0.177 | 4.856000099 | 60059.817 | 640838.048 |
| 0.178 | 4.984000100 | 60399.138 | 644257.472 |
| 0.179 | 5.012000100 | 60738.459 | 647876.896 |
| 0.180 | 5.040000101 | 61077.780 | 651496.320 |
| 0.181 | 5.068000101 | 61417.101 | 655115.744 |
| 0.182 | 5.096000102 | 61756.422 | 658735.168 |
| 0.183 | 5.124000102 | 62095.743 | 662354.592 |
| 0.184 | 5.152000103 | 62435.064 | 665974.016 |
| 0.185 | 5.180000104 | 52774.385 | 669593.440 |
| 0.186 | 5.208000104 | 63113.706 | 763212.864 |
| 0.187 | 5.236000105 | 63453.027 | 676832.288 |
| 0.188 | 5.264000105 | 63792.348 | 680451.712 |
| 0.189 | 5.292000106 | 64131.669 | 684071.136 |
| 0.190 | 5.320000106 | 64470.99 | 687690.560 |
| 0.191 | 5.348000107 | 64810.311 | 691309.984 |
| 0.192 | 5.376000108 | 65149.532 | 694929.408 |
| 0.193 | 5.404000108 | 65488.953 | 698548.832 |
| 0.194 | 5.432000109 | 65828.274 | 702168.256 |
| 0.195 | 5.460000109 | 66167.595 | 705787.680 |
| 0.196 | 5.488000110 | 66506.916 | 709407.104 |
| 0.197 | 5.516000110 | 66846.237 | 713026.528 |
| 0.198 | 5.544000111 | 67185.558 | 716645.952 |
| 0.199 | 5.572000111 | 67524.879 | 720265.376 |
| 0.200 | 5.600000112 | 67864.200 | 723884.800 |
| 0.201 | 5.628000113 | 68203.521 | 727504.224 |
| 0.202 | 5.656000113 | 68542.842 | 731123.648 |
| 0.203 | 5.684000114 | 68882.163 | 734743.072 |
| 0.204 | 5.712000114 | 69221.484 | 738362.496 |
| 0.205 | 5.740000115 | 69560.805 | 741981.920 |
| 0.206 | 5.768000115 | 69900.126 | 745801.344 |
| 0.207 | 5.796000116 | 70239.447 | 749220.768 |

TABLE 3-continued

| | | | |
|---|---|---|---|
| 0.208 | 5.824000116 | 70578.768 | 752840.192 |
| 0.209 | 5.852000117 | 70918.089 | 756459.616 |
| 0.210 | 5.880000118 | 71257.410 | 760079.040 |
| 0.211 | 5.908000118 | 71596.731 | 763698.464 |
| 0.212 | 5.936000119 | 71936.052 | 767317.888 |
| 0.213 | 5.964000119 | 72275.373 | 770937.312 |
| 0.214 | 5.992000120 | 72614.694 | 774556.738 |
| 0.215 | 6.020000120 | 72954.015 | 778178.160 |
| 0.216 | 6.048000121 | 73293.336 | 781795.584 |
| 0.217 | 6.076000122 | 73832.657 | 785415.008 |
| 0.218 | 6.104000122 | 73971.978 | 789034.432 |
| 0.219 | 6.132000123 | 74311.299 | 492653.856 |
| 0.220 | 6.160000123 | 74650.620 | 796372.280 |
| 0.221 | 6.188000124 | 74989.941 | 799892.704 |
| 0.222 | 6.216000124 | 75329.262 | 803512.128 |
| 0.223 | 6.244000125 | 75888.583 | 807161.552 |
| 0.224 | 6.272000125 | 76007.904 | 810750.976 |
| 0.225 | 6.300000126 | 76347.225 | 814370.400 |
| 0.226 | 6.328000127 | 76686.646 | 817989.824 |
| 0.227 | 6.356000127 | 77025.867 | 821609.248 |
| 0.228 | 6.384000128 | 77365.188 | 825228.672 |
| 0.229 | 6.412000128 | 77704.509 | 828848.096 |
| 0.230 | 6.440000129 | 78043.830 | 832467.520 |
| 0.231 | 6.468000129 | 78383.151 | 836086.944 |
| 0.232 | 6.496000130 | 78722.472 | 839706.368 |
| 0.233 | 6.524000130 | 79061.973 | 843325.792 |
| 0.234 | 6.552000131 | 79401.114 | 846945.206 |
| 0.235 | 6.580000132 | 79740.435 | 850564.640 |
| 0.236 | 6.608000132 | 80079.756 | 864184.064 |
| 0.237 | 6.636000133 | 80419.077 | 857803.488 |
| 0.238 | 6.684000133 | 80758.398 | 831422.912 |
| 0.239 | 6.692000134 | 81097.719 | 865042.336 |
| 0.240 | 6.720000134 | 81437.040 | 868661.760 |
| 0.241 | 6.748000135 | 81776.361 | 872281.184 |
| 0.242 | 6.776000136 | 82115.882 | 875900.608 |
| 0.243 | 6.804000136 | 82455.003 | 879520.032 |
| 0.244 | 6.832000137 | 82791.324 | 883139.456 |
| 0.245 | 6.860000137 | 93133.645 | 886759.880 |
| 0.246 | 6.888000138 | 83472.966 | 890378.304 |
| 0.247 | 6.916000138 | 83812.287 | 893997.728 |
| 0.248 | 6.944000139 | 84151.608 | 897617.152 |
| 0.249 | 6.972000139 | 84490.929 | 901236.576 |
| 0.250 | 7.000000140 | 84830.250 | 904856 |
| 0.251 | 7.028000141 | 95169.571 | 908475.424 |
| 0.252 | 7.055000141 | 85508.892 | 912094.848 |
| 0.253 | 7.084000142 | 85848.213 | 915714.272 |
| 0.254 | 7.112000142 | 86187.534 | 919333.696 |
| 0.255 | 7.140000143 | 86526.855 | 922953.120 |
| 0.256 | 7.168000143 | 86866.176 | 926572.544 |
| 0.257 | 7.196000144 | 87205.497 | 930191.968 |
| 0.258 | 7.224000144 | 87544.818 | 933811.392 |
| 0.259 | 7.252000145 | 87884.139 | 937430.816 |
| 0.260 | 7.280000146 | 88223.460 | 941050.240 |
| 0.261 | 7.308000146 | 88562.791 | 944668.664 |
| 0.262 | 7.336000147 | 88902.102 | 948289.088 |
| 0.263 | 7.364000147 | 89241.423 | 951908.512 |
| 0.264 | 7.392000148 | 89580.744 | 955527.936 |
| 0.265 | 7.420000148 | 89920.065 | 959147.360 |
| 0.266 | 7.448000149 | 90259.386 | 962766.784 |
| 0.267 | 7.476000150 | 90598.707 | 966386.208 |
| 0.268 | 7.504000150 | 90938.028 | 970005.632 |
| 0.269 | 7.532000151 | 91277.349 | 973625.056 |
| 0.270 | 7.560000151 | 91616.670 | 977244.480 |
| 0.271 | 7.588000152 | 91955.991 | 980863.904 |
| 0.272 | 7.616000152 | 92295.312 | 984483.328 |
| 0.273 | 7.644000153 | 92634.633 | 988102.752 |
| 0.274 | 7.672000153 | 92973.954 | 991722.176 |
| 0.275 | 7.700000154 | 93313.275 | 995341.600 |
| 0.276 | 7.728000155 | 93652.596 | 998961.024 |
| 0.277 | 7.756000155 | 93991.917 | 1002580.448 |
| 0.278 | 7.784000156 | 94331.238 | 1006199.872 |
| 0.279 | 7.812000156 | 94670.559 | 1009819.296 |
| 0.280 | 7.840000157 | 95009.880 | 1013438.720 |
| 0.281 | 7.868000157 | 95349.201 | 1017058.144 |
| 0.282 | 7.896000158 | 95688.522 | 1020677.568 |
| 0.283 | 7.924000158 | 96027.643 | 1024296.992 |
| 0.284 | 7.952000159 | 96367.164 | 1027916.416 |
| 0.285 | 7.980000160 | 96706.485 | 1031535.840 |
| 0.286 | 8.008000160 | 97045.806 | 1035155.264 |
| 0.287 | 8.036000161 | 97385.127 | 1038774.688 |
| 0.288 | 8.064000161 | 97724.448 | 1042394.112 |
| 0.289 | 8.092000162 | 98063.769 | 1046013.536 |
| 0.290 | 8.120000162 | 98403.090 | 1049632.960 |
| 0.291 | 8.148000163 | 98742.411 | 1053252.384 |
| 0.292 | 8.176000164 | 99081.732 | 1056871.808 |
| 0.293 | 8.204000164 | 99421.053 | 1060491.232 |
| 0.294 | 8.232000165 | 99760.374 | 1064110.656 |
| 0.295 | 8.260000165 | 100099.695 | 1067730.080 |
| 0.296 | 8.288000168 | 100439.016 | 1071349.504 |
| 0.297 | 8.316000166 | 100778.337 | 1072968.928 |
| 0.298 | 8.344000167 | 101117.658 | 1078588.352 |
| 0.299 | 8.372000167 | 101456.979 | 1082207.776 |
| 0.300 | 8.400000168 | 101796.300 | 1085827.200 |
| 0.301 | 8.428000169 | 102135.621 | 1089446.624 |
| 0.302 | 8.456000169 | 102474.942 | 1093066.048 |
| 0.303 | 8.484000170 | 102814.263 | 1096685.472 |
| 0.304 | 8.512000170 | 103153.584 | 1100304.896 |
| 0.305 | 8.640000171 | 103492.905 | 1103924.320 |
| 0.306 | 8.568000171 | 103832.226 | 1107543.744 |
| 0.307 | 8.596000172 | 104171.547 | 1111163.168 |
| 0.308 | 8.624000192 | 104510.868 | 1114782.592 |
| 0.309 | 8.652000173 | 104850.189 | 1118402.016 |
| 0.310 | 8.680000174 | 105189.510 | 1122021.440 |
| 0.311 | 8.708000174 | 105528.831 | 1125640.864 |
| 0.312 | 8.836000175 | 105868.152 | 1129260.288 |
| 0.313 | 8.764000175 | 106207.473 | 1132879.712 |
| 0.314 | 8.792000176 | 106546.794 | 1136499.136 |
| 0.315 | 8.820000176 | 106886.115 | 1140118.560 |
| 0.316 | 8.848000177 | 107225.436 | 1143737.984 |
| 0.317 | 8.876000178 | 107564.757 | 1147357.408 |
| 0.318 | 8.904000178 | 107904.078 | 1150976.832 |
| 0.319 | 8.932000179 | 108243.399 | 1154596.256 |
| 0.320 | 8.960000179 | 108582.720 | 1158215.680 |
| 0.321 | 8.988000180 | 108922.041 | 1161835.104 |
| 0.322 | 9.016000180 | 109261.362 | 1165454.528 |
| 0.323 | 9.044000181 | 109600.683 | 1169073.952 |
| 0.324 | 9.072000181 | 109940.004 | 1172693.376 |
| 0.325 | 9.100000182 | 110279.325 | 1176312.800 |
| 0.326 | 9.128000183 | 110618.646 | 1179932.224 |
| 0.327 | 9.156000183 | 110957.967 | 1183551.648 |
| 0.328 | 9.184000184 | 111297.288 | 1187171.072 |
| 0.329 | 9.212000184 | 111636.609 | 1190790.496 |
| 0.330 | 9.240000185 | 111975.930 | 1194409.920 |
| 0.331 | 9.268000185 | 112315.251 | 1198029.344 |
| 0.332 | 9.296000186 | 112654.572 | 1201648.768 |
| 0.333 | 9.324000186 | 112993.893 | 1205268.192 |
| 0.334 | 9.352000187 | 113333.214 | 1208887.616 |
| 0.335 | 9.380000188 | 113672.535 | 1212507.040 |
| 0.336 | 9.408000188 | 114011.856 | 1216126.464 |
| 0.337 | 9.436000189 | 114351.177 | 1219745.888 |
| 0.338 | 9.464000189 | 114890.498 | 1223365.312 |
| 0.339 | 9.492000190 | 115029.819 | 1226984.736 |
| 0.340 | 9.520000190 | 115369.140 | 1230604.160 |
| 0.341 | 9.548000191 | 115705.461 | 1234223.584 |
| 0.342 | 8.576000192 | 116047.782 | 1237843.008 |
| 0.343 | 9.604000192 | 116387.103 | 1241462.432 |
| 0.344 | 9.632000193 | 116726.424 | 1245081.856 |
| 0.345 | 9.680000193 | 117065.745 | 1248701.280 |
| 0.346 | 9.688000194 | 117405.086 | 1252320.704 |
| 0.347 | 9.716000194 | 117744.387 | 1255940.128 |
| 0.348 | 9.744000195 | 118083.708 | 1259559.552 |
| 0.349 | 9.772000195 | 118423.029 | 1263178.976 |
| 0.350 | 9.800000196 | 118762.350 | 1266798.400 |
| 0.351 | 9.828000197 | 119101.671 | 1270417.824 |
| 0.352 | 9.858000197 | 119440.992 | 1274037.248 |
| 0.353 | 9.884000198 | 119780.313 | 1277656.672 |
| 0.354 | 9.912000198 | 120119.634 | 1281276.096 |
| 0.355 | 9.940000199 | 120458.955 | 1284895.520 |
| 0.356 | 9.968000199 | 120798.276 | 1288514.944 |
| 0.357 | 9.996000200 | 121137.597 | 1292134.368 |
| 0.358 | 10.024000200 | 121476.918 | 1295759.792 |
| 0.359 | 10.052000200 | 121816.239 | 1299373.216 |
| 0.360 | 10.080000200 | 122155.560 | 1302992.640 |
| 0.361 | 10.108000200 | 122494.881 | 1306612.064 |
| 0.362 | 10.138000200 | 122834.202 | 1310231.488 |
| 0.363 | 10.164000200 | 123173.523 | 1313850.912 |
| 0.364 | 10.192000200 | 123512.844 | 1317470.336 |
| 0.365 | 10.220000200 | 123852.165 | 1321089.760 |
| 0.366 | 10.248000200 | 124191.486 | 1324709.184 |
| 0.367 | 10.276000210 | 124530.807 | 1328328.608 |

TABLE 3-continued

| | | | |
|---|---|---|---|
| 0.368 | 10.304000210 | 124870.128 | 1331948.032 |
| 0.369 | 10.332000210 | 125209.449 | 1335567.456 |
| 0.370 | 10.360000210 | 125548.770 | 1339186.880 |
| 0.371 | 10.388000210 | 125888.091 | 1342806.304 |
| 0.372 | 10.416000210 | 126227.412 | 1346425.728 |
| 0.373 | 10.444000210 | 126566.733 | 1650045.152 |
| 0.374 | 10.472000210 | 126906.054 | 1353664.576 |
| 0.375 | 10.500000210 | 127245.375 | 1357284.000 |
| 0.376 | 10.528000210 | 127584.696 | 1360903.424 |
| 0.377 | 10.558000210 | 127924.017 | 1364522.848 |
| 0.378 | 10.584000210 | 128263.338 | 1368142.272 |
| 0.379 | 10.612000210 | 128602.659 | 1371761.696 |
| 0.380 | 10.640000210 | 128941.980 | 1375381.120 |
| 0.381 | 10.66800021 | 129281.301 | 1379000.544 |
| 0.382 | 10.969000210 | 129620.622 | 1382619.968 |
| 0.383 | 10.724000210 | 129959.943 | 1386239.392 |
| 0.384 | 10.752000220 | 130299.264 | 1389858.815 |
| 0.385 | 10.780000220 | 130638.585 | 1393478.240 |
| 0.386 | 10.808000220 | 130977.906 | 1397097.664 |
| 0.387 | 10.838000220 | 131317.227 | 1400717.088 |
| 0.388 | 10.864000220 | 131656.548 | 1404336.512 |
| 0.389 | 10.892000220 | 131995.869 | 1407955.936 |
| 0.390 | 10.920000220 | 132335.190 | 1411575.360 |
| 0.391 | 10.948000220 | 132674.511 | 1415194.784 |
| 0.392 | 10.976000220 | 133013.832 | 1418814.208 |
| 0.393 | 11.004000220 | 133353.153 | 1422433.632 |
| 0.394 | 11.032000220 | 133682.474 | 1426053.058 |
| 0.395 | 11.060000220 | 134031.795 | 1429672.480 |
| 0.396 | 11.088000220 | 134371.116 | 1433291.904 |
| 0.397 | 11.116000220 | 134710.437 | 1436911.328 |
| 0.398 | 11.144000220 | 135049.758 | 1440530.762 |
| 0.399 | 11.172000220 | 135389.079 | 1444150.176 |
| 0.400 | 11.200000220 | 135728.400 | 1447769.600 |
| 0.401 | 11.228000220 | 136067.721 | 1451389.024 |
| 0.402 | 11.256000230 | 136407.042 | 1455008.448 |
| 0.403 | 11.274000230 | 136746.363 | 1458627.872 |
| 0.404 | 11.312000230 | 137085.684 | 1462247.296 |
| 0.405 | 11.340002300 | 137425.005 | 1465886.720 |
| 0.406 | 11.368000230 | 137764.326 | 1469486.144 |
| 0.407 | 11.396000230 | 138103.647 | 1473105.568 |
| 0.408 | 11.424000230 | 138442.968 | 1476724.992 |
| 0.409 | 11.452000230 | 138782.289 | 1480344.416 |
| 0.410 | 11.480000230 | 139121.610 | 1483963.840 |
| 0.411 | 11.508000230 | 139460.931 | 1487583.264 |
| 0.412 | 11.536000230 | 139800.252 | 1491202.688 |
| 0.413 | 11.564000230 | 140139.573 | 1494822.112 |
| 0.414 | 11.692000230 | 140478.894 | 1498441.536 |
| 0.415 | 11.620000230 | 170818.215 | 1502060.960 |
| 0.416 | 11.648000230 | 141157.536 | 1505680.384 |
| 0.417 | 11.676000230 | 141496.857 | 1509299.808 |
| 0.418 | 11.704000230 | 141836.178 | 1512919.232 |
| 0.419 | 11.732000230 | 142175.499 | 1518538.656 |
| 0.420 | 11.760000240 | 142514.820 | 1520158.080 |
| 0.421 | 11.788000240 | 142854.141 | 1523777.504 |
| 0.422 | 11.816000240 | 143193.462 | 1527396.928 |
| 0.423 | 11.844000240 | 143532.783 | 1531016.352 |
| 0.424 | 11.872000240 | 143872.104 | 1534635.776 |
| 0.425 | 11.900000240 | 144211.425 | 1538255.200 |
| 0.426 | 11.928000240 | 144550.746 | 1541874.624 |
| 0.427 | 11.956000240 | 144890.067 | 1545494.048 |
| 0.428 | 11.984000240 | 145229.388 | 1549113.482 |
| 0.429 | 12.012000240 | 145568.709 | 1552732.896 |
| 0.430 | 12.040000240 | 145906.030 | 1556352.320 |
| 0.431 | 12.068000240 | 146247.351 | 1559971.744 |
| 0.432 | 12.096000240 | 146586.672 | 1563691.168 |
| 0.433 | 12.124000240 | 146925.993 | 1567210.592 |
| 0.434 | 12.152000240 | 147265.314 | 1570830.018 |
| 0.435 | 12.180000240 | 147604.635 | 1574449.440 |
| 0.436 | 12.208000240 | 147943.956 | 1578068.864 |
| 0.437 | 12.236000240 | 148283.277 | 1581688.288 |
| 0.438 | 12.264000240 | 148622.598 | 1585307.712 |
| 0.439 | 12.282000250 | 148961.919 | 1588927.136 |
| 0.440 | 12.320000250 | 149301.240 | 1592546.560 |
| 0.441 | 12.348000250 | 149640.561 | 1596165.984 |
| 0.442 | 12.386000250 | 149979.408 | 1599785.408 |
| 0.443 | 12.404000250 | 150319.203 | 1603404.832 |
| 0.444 | 12.432000250 | 150658.524 | 1607024.256 |
| 0.445 | 12.460000250 | 150997.845 | 1610643.680 |
| 0.446 | 12.488000250 | 151337.166 | 1614263.104 |
| 0.447 | 12.516000250 | 151676.487 | 1617882.528 |
| 0.448 | 12.544000250 | 152015.808 | 1621501.952 |
| 0.449 | 12.572000250 | 152355.129 | 1625121.376 |
| 0.450 | 12.600000250 | 152694.450 | 1628740.800 |
| 0.451 | 12.628000250 | 153033.771 | 1632360.224 |
| 0.452 | 12.656000250 | 153373.092 | 1635979.648 |
| 0.453 | 12.684000250 | 153712.413 | 1639599.072 |
| 0.454 | 12.712000250 | 154051.734 | 1643218.496 |
| 0.455 | 12.740000250 | 154391.055 | 1646837.920 |
| 0.456 | 12.768000260 | 154730.376 | 1650457.344 |
| 0.457 | 12.796000260 | 155069.697 | 1654076.768 |
| 0.458 | 12.824000260 | 155409.018 | 1657696.792 |
| 0.459 | 12.852000260 | 155748.339 | 1661315.616 |
| 0.460 | 12.880000260 | 156087.660 | 1664935.040 |
| 0.461 | 12.908000260 | 156426.981 | 1668554.464 |
| 0.462 | 12.936000260 | 156766.302 | 1672173.888 |
| 0.463 | 12.964000260 | 157105.523 | 1675793.312 |
| 0.464 | 12.992000260 | 157444.944 | 1679412.736 |
| 0.465 | 13.020000260 | 157784.265 | 1383032.160 |
| 0.466 | 13.048000260 | 158123.586 | 1686651.584 |
| 0.467 | 13.076000260 | 128462.907 | 1690271.008 |
| 0.468 | 13.104000260 | 158802.228 | 1693890.432 |
| 0.469 | 13.132000260 | 159141.549 | 1697509.856 |
| 0.470 | 13.160000260 | 159480.870 | 1701129.280 |
| 0.471 | 13.188000260 | 159820.191 | 1704748.704 |
| 0.472 | 13.216000260 | 160159.512 | 1708368.128 |
| 0.473 | 13.244000260 | 160498.833 | 1711987.552 |
| 0.474 | 13.272000270 | 160838.154 | 1715606.976 |
| 0.475 | 13.300000270 | 161177.475 | 1719226.400 |
| 0.476 | 13.328000270 | 161516.795 | 1722845.824 |
| 0.477 | 13.356000270 | 161856.117 | 1726465.248 |
| 0.478 | 13.384000270 | 162195.438 | 1730084.672 |
| 0.479 | 13.412000270 | 162534.759 | 1733704.096 |
| 0.480 | 13.440000270 | 162874.080 | 1737323.520 |
| 0.481 | 13.468000270 | 163213.401 | 1740942.944 |
| 0.482 | 13.496000270 | 163552.722 | 1744562.368 |
| 0.483 | 13.524000270 | 163892.043 | 1748181.792 |
| 0.484 | 13.552000270 | 164231.364 | 1751801.216 |
| 0.485 | 13.580000270 | 164570.685 | 1755420.640 |
| 0.486 | 13.608000270 | 164910.006 | 1759040.064 |
| 0.487 | 13.636000270 | 165249.327 | 1762659.488 |
| 0.488 | 13.664000270 | 165588.648 | 1766276.810 |
| 0.489 | 13.692000270 | 165927.969 | 1769898.336 |
| 0.490 | 13.720000270 | 166287.29 | 1773517.760 |
| 0.491 | 13.748000270 | 166606.611 | 1777137.184 |
| 0.492 | 13.778000280 | 166945.932 | 1780756.608 |
| 0.493 | 13.804000280 | 167285.253 | 1784376.032 |
| 0.494 | 13.832000280 | 167624.574 | 1787995.456 |
| 0.495 | 13.860000280 | 167963.895 | 1791614.880 |
| 0.496 | 13.888000280 | 168303.216 | 1795234.304 |
| 0.497 | 13.916000280 | 168642.537 | 1798853.728 |
| 0.498 | 13.944000280 | 168981.858 | 1802473.152 |
| 0.499 | 13.972000280 | 169321.179 | 1806092.567 |
| 0.500 | 14.000000280 | 169660.500 | 1809712.000 |
| 0.501 | 14.028000280 | 169999.821 | 1813331.424 |
| 0.502 | 14.056000280 | 170339.142 | 1816950.848 |
| 0.503 | 14.084000280 | 170678.463 | 1820570.272 |
| 0.504 | 14.112000280 | 171017.784 | 1824189.696 |
| 0.505 | 14.140000280 | 171367.105 | 1827809.120 |
| 0.506 | 14.168000280 | 171696.426 | 1831428.544 |
| 0.507 | 14.196000280 | 172035.747 | 1835047.968 |
| 0.508 | 14.224000280 | 172375.068 | 1838667.392 |
| 0.509 | 14.252000290 | 172714.389 | 1842286.816 |
| 0.510 | 14.280000290 | 173053.710 | 1845906.240 |
| 0.511 | 14.308000290 | 173393.031 | 1849525.664 |
| 0.512 | 14.336000290 | 173732.352 | 1853145.088 |
| 0.513 | 14.364000290 | 174071.673 | 1856764.512 |
| 0.514 | 14.392000290 | 174410.994 | 1860383.936 |
| 0.515 | 14.420000290 | 174750.315 | 1864003.360 |
| 0.516 | 14.448000290 | 175089.636 | 1867622.784 |
| 0.517 | 14.476000290 | 175428.957 | 1871242.208 |
| 0.518 | 14.504000290 | 175768.278 | 1874861.632 |
| 0.519 | 14.532000290 | 176107.599 | 1878481.058 |
| 0.520 | 14.560000290 | 176446.920 | 1882100.480 |
| 0.521 | 14.588000290 | 176786.241 | 1885719.904 |
| 0.522 | 14.616000290 | 177125.562 | 1889339.328 |
| 0.523 | 14.644000290 | 177464.883 | 1892958.752 |
| 0.524 | 14.672000290 | 177804.204 | 1896578.176 |
| 0.525 | 14.700000290 | 178143.525 | 1900197.600 |
| 0.526 | 14.728000290 | 178482.846 | 1903817.024 |
| 0.527 | 14.756000300 | 178822.167 | 1907436.448 |

TABLE 3-continued

| | | | |
|---|---|---|---|
| 0.528 | 14.784000300 | 179161.488 | 1911055.872 |
| 0.529 | 14.812000300 | 179500.809 | 1914675.296 |
| 0.530 | 14.840000300 | 179840.130 | 1918294.720 |
| 0.531 | 14.868000300 | 180179.451 | 1921914.144 |
| 0.532 | 14.896000300 | 180518.772 | 1925533.568 |
| 0.533 | 14.924000300 | 180858.093 | 1929152.992 |
| 0.534 | 14.952000300 | 181197.414 | 1932772.416 |
| 0.535 | 14.980000300 | 181536.735 | 1936391.840 |
| 0.536 | 15.005000300 | 181876.056 | 1940011.264 |
| 0.537 | 15.036000300 | 182215.377 | 1943630.688 |
| 0.538 | 15.064000300 | 182554.698 | 1947250.112 |
| 0.539 | 15.092000300 | 182894.019 | 1950869.536 |
| 0.540 | 15.120000300 | 183233.340 | 1954488.960 |
| 0.541 | 15.148000300 | 183572.661 | 1958108.384 |
| 0.542 | 15.176000300 | 183911.982 | 1961727.808 |
| 0.543 | 15.204000300 | 184251.303 | 1965347.232 |
| 0.544 | 15.232000300 | 184590.624 | 1968966.656 |
| 0.545 | 15.260000310 | 184929.945 | 1972586.080 |
| 0.546 | 15.288000310 | 185269.266 | 1976205.504 |
| 0.547 | 15.316000310 | 185608.587 | 1979824.928 |
| 0.548 | 15.344000310 | 185947.908 | 1983444.352 |
| 0.549 | 15.372000310 | 186287.229 | 1987063.776 |
| 0.550 | 15.400000310 | 186626.550 | 1990683.200 |
| 0.551 | 15.428000310 | 186965.871 | 1994302.624 |
| 0.552 | 15.456000310 | 187305.192 | 1997922.048 |
| 0.553 | 15.484000310 | 187644.513 | 2001541.472 |
| 0.554 | 15.512000310 | 187983.834 | 2005160.896 |
| 0.555 | 15.540000310 | 188323.155 | 2008780.320 |
| 0.556 | 15.568000310 | 188662.476 | 2012399.744 |
| 0.557 | 15.596000310 | 189001.797 | 2016019.168 |
| 0.558 | 15.624000310 | 189341.118 | 2019638.592 |
| 0.559 | 15.652000310 | 189680.439 | 2023258.016 |
| 0.560 | 15.680000310 | 190019.760 | 2026877.440 |
| 0.561 | 15.708000310 | 190359.081 | 2030496.864 |
| 0.562 | 15.736000310 | 190698.402 | 2034116.288 |
| 0.563 | 15.764000320 | 191037.723 | 2037735.712 |
| 0.564 | 15.792000320 | 191377.044 | 2041355.136 |
| 0.565 | 15.820000320 | 191716.385 | 2044974.560 |
| 0.566 | 15.848000320 | 192055.686 | 2048593.984 |
| 0.567 | 15.876000320 | 192395.007 | 2052213.408 |
| 0.568 | 15.904000320 | 192734.328 | 2055832.832 |
| 0.569 | 15.932000320 | 193073.649 | 2059452.256 |
| 0.570 | 15.960000320 | 193412.970 | 2063071.680 |
| 0.571 | 15.988000320 | 193752.291 | 2066691.104 |
| 0.572 | 16.016000320 | 194091.612 | 2070310.528 |
| 0.573 | 16.044000320 | 194430.933 | 2073929.952 |
| 0.574 | 16.072000320 | 194770.254 | 2077549.376 |
| 0.575 | 16.100000320 | 195109.575 | 2081168.800 |
| 0.576 | 16.128000320 | 195448.896 | 2084788.224 |
| 0.577 | 16.156000320 | 195788.217 | 2088407.648 |
| 0.578 | 16.184000320 | 196127.538 | 2092027.072 |
| 0.579 | 16.212000320 | 196466.859 | 2095646.496 |
| 0.580 | 16.240000320 | 196806.180 | 2099265.920 |
| 0.581 | 16.268000320 | 197145.501 | 2102885.344 |
| 0.582 | 16.296000330 | 197484.822 | 2106504.768 |
| 0.583 | 16.324000330 | 197824.143 | 2110124.192 |
| 0.584 | 16.352000330 | 198163.434 | 2113743.616 |
| 0.585 | 16.380000330 | 198502.785 | 2117363.040 |
| 0.586 | 16.408000330 | 198842.106 | 2120982.464 |
| 0.587 | 16.436000330 | 199181.427 | 2124601.888 |
| 0.588 | 16.464000330 | 199620.748 | 2128221.312 |
| 0.589 | 16.492000330 | 199860.069 | 2131840.736 |
| 0.590 | 16.520000330 | 200199.390 | 2135460.160 |
| 0.591 | 16.548000330 | 200538.711 | 2139079.581 |
| 0.592 | 16.576000330 | 200878.032 | 2142699.008 |
| 0.593 | 16.604000330 | 201217.353 | 2146318.432 |
| 0.594 | 16.632000330 | 201556.674 | 2149937.856 |
| 0.595 | 16.660000330 | 201895.995 | 2153557.280 |
| 0.596 | 16.688000330 | 202235.316 | 2157176.704 |
| 0.597 | 16.716000330 | 202574.634 | 2160796.128 |
| 0.598 | 16.744000330 | 202913.958 | 2164415.552 |
| 0.599 | 16.772000340 | 203253.279 | 2168034.976 |
| 0.600 | 16.800000340 | 203592.600 | 2171654.400 |
| 0.601 | 16.828000340 | 203931.921 | 2175273.824 |
| 0.602 | 16.856000340 | 204271.242 | 2178893.248 |
| 0.603 | 16.884000340 | 204610.563 | 2182512.672 |
| 0.604 | 16.912000340 | 204949.884 | 2188132.096 |
| 0.605 | 16.940000340 | 205289.205 | 2189751.520 |
| 0.606 | 16.968000340 | 205628.526 | 2193370.944 |
| 0.607 | 16.996000340 | 205976.847 | 2196990.368 |
| 0.608 | 17.024000340 | 206307.168 | 2200609.792 |
| 0.609 | 17.052000340 | 206646.489 | 2204229.216 |
| 0.610 | 17.080000340 | 206985.810 | 2207848.640 |
| 0.611 | 17.108000340 | 207325.131 | 2211468.064 |
| 0.612 | 17.136000340 | 207664.452 | 2215087.488 |
| 0.613 | 17.164000340 | 208003.773 | 2218706.912 |
| 0.614 | 17.192000340 | 208343.094 | 2222326.336 |
| 0.615 | 17.220000340 | 208682.415 | 2225945.760 |
| 0.616 | 17.248000340 | 209021.736 | 2229565.184 |
| 0.617 | 17.276000350 | 209361.057 | 2233184.608 |
| 0.618 | 17.304000350 | 209700.378 | 2236804.032 |
| 0.619 | 17.332000350 | 210039.699 | 2240423.456 |
| 0.620 | 17.360000350 | 210379.020 | 2244042.880 |
| 0.621 | 17.388000350 | 210718.341 | 2247662.304 |
| 0.622 | 17.41600035 | 211057.662 | 2251281.728 |
| 0.623 | 17.444000350 | 211396.983 | 2254901.152 |
| 0.624 | 17.472000350 | 211736.304 | 2258520.576 |
| 0.625 | 17.500000350 | 212075.625 | 2262140.000 |
| 0.626 | 17.528000350 | 212414.946 | 2265759.424 |
| 0.627 | 17.550003500 | 212754.267 | 2269378.848 |
| 0.628 | 17.584000350 | 213093.588 | 2272998.272 |
| 0.629 | 17.612000350 | 213432.909 | 2276617.696 |
| 0.630 | 17.640000350 | 213772.230 | 2280237.120 |
| 0.631 | 17.66800035 | 214111.551 | 2283856.544 |
| 0.632 | 17.696000350 | 214450.872 | 2287475.968 |
| 0.633 | 17.724000350 | 214790.193 | 2291095.392 |
| 0.634 | 17.752000360 | 215139.514 | 2294714.816 |
| 0.635 | 17.780000360 | 215468.835 | 2298334.240 |
| 0.636 | 17.808000360 | 215808.156 | 2301953.664 |
| 0.637 | 17.836000360 | 216147.477 | 2305573.088 |
| 0.638 | 17.864000360 | 216486.798 | 2309192.512 |
| 0.639 | 17.892000360 | 216826.119 | 231281.936 |
| 0.640 | 17.920000360 | 217165.440 | 2316431.360 |
| 0.641 | 17.940003600 | 215704.761 | 2320050.784 |
| 0.642 | 17.976000360 | 217844.082 | 2323670.208 |
| 0.643 | 18.004000360 | 218183.403 | 2327289.632 |
| 0.644 | 18.032000360 | 218522.724 | 2330909.056 |
| 0.645 | 18.060000360 | 218862.045 | 2334528.460 |
| 0.646 | 18.088000360 | 219201.366 | 2338147.904 |
| 0.647 | 18.116000360 | 219540.687 | 2341767.328 |
| 0.648 | 18.144000360 | 219880.008 | 2345386.752 |
| 0.649 | 18.172000360 | 220219.329 | 2349006.176 |
| 0.650 | 18.200000360 | 220558.650 | 2352825.600 |
| 0.651 | 18.228000360 | 220897.971 | 2356245.024 |
| 0.652 | 18.256000370 | 221237.292 | 2359867.448 |
| 0.653 | 18.284000370 | 221576.613 | 2363483.872 |
| 0.654 | 18.312000370 | 221915.934 | 2367103.296 |
| 0.655 | 18.340000370 | 222255.255 | 2370722.720 |
| 0.656 | 18.368000370 | 222594.576 | 2374342.144 |
| 0.657 | 18.396000370 | 222933.897 | 2377961.588 |
| 0.658 | 18.424000370 | 223273.218 | 2381580.992 |
| 0.659 | 18.452000370 | 223612.539 | 2385200.416 |
| 0.660 | 18.480000370 | 223951.860 | 2388819.840 |
| 0.661 | 18.508000370 | 224291.181 | 2392439.264 |
| 0.662 | 18.536000370 | 224630.502 | 2396058.888 |
| 0.663 | 18.564000370 | 224969.823 | 2399678.112 |
| 0.664 | 18.592000370 | 225309.144 | 2403297.536 |
| 0.665 | 18.620000370 | 225648.465 | 2406916.960 |
| 0.666 | 18.648000370 | 225987.786 | 2410538.384 |
| 0.667 | 18.676000370 | 226327.107 | 2414155.808 |
| 0.668 | 18.704000370 | 226666.428 | 2417775.232 |
| 0.669 | 18.732000370 | 227005.749 | 2421394.858 |
| 0.670 | 18.760000380 | 227345.070 | 2425014.080 |
| 0.671 | 18.788000380 | 227684.391 | 2428633.504 |
| 0.672 | 18.816000380 | 228023.712 | 2432252.928 |
| 0.673 | 18.844000380 | 228363.033 | 2435872.352 |
| 0.674 | 18.87200038 | 228702.354 | 2439491.776 |
| 0.675 | 18.900000380 | 229041.675 | 2443111.200 |
| 0.676 | 18.928000380 | 229380.996 | 2446730.624 |
| 0.677 | 18.958000380 | 229720.317 | 2460350.048 |
| 0.678 | 18.984000380 | 230059.638 | 2453969.472 |
| 0.679 | 19.012000380 | 230398.959 | 2457588.896 |
| 0.680 | 19.040000380 | 230738.280 | 2461208.320 |
| 0.681 | 19.068000380 | 321077.601 | 2464827.744 |
| 0.682 | 19.096000380 | 231416.922 | 2468447.168 |
| 0.683 | 19.124000380 | 231756.243 | 2472066.592 |
| 0.684 | 19.152000380 | 232095.564 | 2475686.016 |
| 0.685 | 19.180000380 | 232434.885 | 2479305.110 |
| 0.686 | 19.208000380 | 232774.206 | 2482924.864 |
| 0.687 | 19.236000380 | 233113.527 | 2486544.288 |

TABLE 3-continued

| | | | |
|---|---|---|---|
| 0.688 | 19.264000390 | 233452.848 | 2490163.712 |
| 0.689 | 19.292000390 | 233792.169 | 2493783.136 |
| 0.690 | 19.320000390 | 234131.490 | 2497402.560 |
| 0.691 | 19.348000390 | 234470.811 | 2501021.984 |
| 0.692 | 19.376000390 | 234810.132 | 2504641.408 |
| 0.693 | 19.404000390 | 235149.453 | 2508260.832 |
| 0.694 | 19.432000390 | 235488.774 | 2511880.256 |
| 0.695 | 19.46000039 | 235828.095 | 2515499.680 |
| 0.696 | 19.488000390 | 236167.416 | 2519119.104 |
| 0.697 | 19.516000390 | 236506.737 | 2520738.528 |
| 0.698 | 19.544000390 | 236845.058 | 2526357.952 |
| 0.699 | 19.572000390 | 237185.379 | 2529977.376 |
| 0.700 | 19.600000390 | 237524.700 | 2533596.800 |
| 0.701 | 19.628000390 | 237864.021 | 2537216.224 |
| 0.702 | 19.656000390 | 238203.342 | 2540835.648 |
| 0.703 | 19.684000390 | 238542.663 | 2544455.072 |
| 0.704 | 19.712000390 | 238881.984 | 2548074.496 |
| 0.705 | 19.740000390 | 239221.305 | 2551693.920 |
| 0.706 | 19.768000400 | 239560.626 | 2555313.344 |
| 0.707 | 19.796000400 | 239899.947 | 2558932.768 |
| 0.708 | 19.824000400 | 240239.268 | 2562552.192 |
| 0.709 | 19.852000400 | 240578.589 | 2566171.616 |
| 0.710 | 19.880000400 | 240917.910 | 2569791.040 |
| 0.711 | 19.908000400 | 241257.231 | 2573410.464 |
| 0.712 | 19.936000400 | 241596.552 | 2577029.888 |
| 0.713 | 19.964000400 | 241935.873 | 2580649.312 |
| 0.714 | 19.992000400 | 242275.194 | 2584268.736 |
| 0.715 | 20.020000400 | 242614.515 | 2587888.160 |
| 0.716 | 20.048000400 | 242953.836 | 2591507.584 |
| 0.717 | 20.086000400 | 243293.157 | 2595127.008 |
| 0.718 | 20.104000400 | 243632.478 | 2598746.432 |
| 0.719 | 20.132000400 | 243971.799 | 2602365.856 |
| 0.720 | 20.160000400 | 244311.120 | 2605985.280 |
| 0.721 | 20.188000400 | 244650.441 | 2609604.704 |
| 0.722 | 20.216000400 | 244989.762 | 2613224.128 |
| 0.723 | 20.244000200 | 245329.083 | 2616843.552 |
| 0.724 | 20.272000410 | 245668.404 | 2820482.976 |
| 0.725 | 20.300000410 | 246007.725 | 2624082.400 |
| 0.726 | 20.328000410 | 246347.046 | 2627701.842 |
| 0.727 | 20.356000410 | 246686.367 | 2631321.248 |
| 0.728 | 20.384000410 | 247025.688 | 2634940.672 |
| 0.729 | 20.412000410 | 247365.009 | 2638580.096 |
| 0.730 | 20.440000410 | 247704.330 | 2642179.520 |
| 0.731 | 20.468000410 | 248043.651 | 2645798.844 |
| 0.732 | 20.496000410 | 248382.972 | 2649418.368 |
| 0.733 | 20.524000410 | 248722.293 | 2653037.792 |
| 0.734 | 20.552000410 | 249061.614 | 2856657.216 |
| 0.735 | 20.580000410 | 249400.935 | 2660276.640 |
| 0.736 | 20.608000410 | 249740.256 | 2663896.064 |
| 0.737 | 20.636000410 | 250079.577 | 2667515.488 |
| 0.738 | 20.651000410 | 250418.898 | 2671134.912 |
| 0.739 | 20.692000410 | 250758.219 | 2674754.336 |
| 0.740 | 20.720000410 | 251097.540 | 2678373.760 |
| 0.741 | 20.748000410 | 251436.861 | 2681993.184 |
| 0.742 | 20.776000420 | 251776.182 | 2685612.608 |
| 0.743 | 20.804000420 | 252115.503 | 2689232.032 |
| 0.744 | 20.832000420 | 252151.824 | 2692851.458 |
| 0.745 | 20.860000420 | 252794.145 | 2696470.880 |
| 0.746 | 20.888000420 | 253133.466 | 2700090.304 |
| 0.747 | 20.916000420 | 253472.787 | 2703709.728 |
| 0.748 | 20.944000420 | 253812.108 | 2707329.152 |
| 0.749 | 20.972000420 | 254151.429 | 2710948.576 |
| 0.750 | 21.000000420 | 254490.750 | 2714588.000 |
| 0.751 | 21.028000420 | 254830.071 | 2718187.424 |
| 0.752 | 21.056000420 | 155169.392 | 2721806.848 |
| 0.753 | 21.084000420 | 255508.713 | 2725426.272 |
| 0.754 | 21.112000420 | 255848.034 | 2729045.696 |
| 0.755 | 21.140000420 | 256187.355 | 2732665.120 |
| 0.756 | 21.168000420 | 258526.676 | 2736284.544 |
| 0.757 | 21.196000420 | 258865.997 | 2739903.968 |
| 0.758 | 21.224000420 | 257205.318 | 2743523.392 |
| 0.759 | 21.252000430 | 257544.639 | 2747142.816 |
| 0.760 | 21.280000430 | 257883.960 | 2750762.240 |
| 0.761 | 21.308000430 | 258223.281 | 2754381.664 |
| 0.762 | 21.336000430 | 258562.602 | 2758001.088 |
| 0.763 | 21.364000430 | 258901.923 | 2761620.512 |
| 0.764 | 21.392000430 | 259241.244 | 2765239.936 |
| 0.765 | 21.420000430 | 259580.565 | 2768859.360 |
| 0.766 | 21.448000430 | 259919.886 | 2772478.784 |
| 0.767 | 21.47600043 | 260259.207 | 2776096.206 |
| 0.768 | 21.504000430 | 260598.528 | 2779717.632 |
| 0.769 | 21.532000430 | 260937.849 | 2783337.056 |
| 0.770 | 21.580000430 | 261277.170 | 2786956.480 |
| 0.771 | 21.588000430 | 261616.491 | 2790575.904 |
| 0.772 | 21.616000430 | 261955.812 | 2794195.328 |
| 0.773 | 21.644000430 | 262295.133 | 2797814.752 |
| 0.774 | 21.672000430 | 262634.454 | 2801434.176 |
| 0.775 | 21.700000430 | 262973.775 | 2805053.600 |
| 0.776 | 21.728000430 | 263313.096 | 2808673.024 |
| 0.777 | 21.756000440 | 263652.417 | 2812292.448 |
| 0.778 | 21.784000440 | 263991.738 | 2815911.872 |
| 0.779 | 21.812000440 | 264331.059 | 2819531.296 |
| 0.780 | 21.840000440 | 264670.380 | 2823150.720 |
| 0.781 | 21.868000440 | 265009.701 | 2826770.144 |
| 0.782 | 21.896000440 | 265349.002 | 2830389.568 |
| 0.783 | 21.924000440 | 265688.343 | 2834008.992 |
| 0.784 | 21.952000440 | 266027.664 | 2837628.416 |
| 0.785 | 21.980000440 | 266366.985 | 2841247.840 |
| 0.786 | 22.008000440 | 266706.306 | 2844867.264 |
| 0.787 | 22.036000440 | 267045.627 | 2848486.688 |
| 0.788 | 22.064000440 | 267384.948 | 2852106.112 |
| 0.789 | 22.092000440 | 267724.269 | 2855725.538 |
| 0.790 | 22.120000440 | 268063.59 | 2859344.960 |
| 0.791 | 22.148000440 | 268402.911 | 2862964.384 |
| 0.792 | 22.176000440 | 268742.232 | 2866583.808 |
| 0.793 | 22.204000440 | 269081.553 | 2870203.232 |
| 0.794 | 22.232000440 | 269420.874 | 2873822.656 |
| 0.795 | 22.260000450 | 289760.195 | 2877442.080 |
| 0.796 | 22.288000450 | 270099.516 | 2881061.504 |
| 0.797 | 22.316000450 | 270438.837 | 2884680.928 |
| 0.798 | 22.344000450 | 270778.158 | 2888300.352 |
| 0.799 | 22.372000450 | 271117.479 | 2891919.766 |
| 0.800 | 22.400000450 | 271456.800 | 2895539.200 |
| 0.801 | 22.428000450 | 271796.121 | 2899158.624 |
| 0.802 | 22.456000450 | 272135.442 | 2902778.048 |
| 0.803 | 22.484000450 | 272474.763 | 2906397.472 |
| 0.804 | 22.512000450 | 272814.084 | 2910016.896 |
| 0.805 | 22.540000450 | 273153.405 | 2913636.320 |
| 0.806 | 22.568000450 | 273492.726 | 2917255.744 |
| 0.807 | 22.596000450 | 273832.047 | 2920875.168 |
| 0.808 | 22.624000450 | 274171.368 | 2924494.592 |
| 0.809 | 22.652000450 | 274510.689 | 2928114.016 |
| 0.810 | 22.680000450 | 274850.010 | 2931733.440 |
| 0.811 | 22.708000450 | 275189.331 | 2935352.864 |
| 0.812 | 22.736000450 | 275528.652 | 2938972.288 |
| 0.813 | 22.784000450 | 275667.973 | 2942591.712 |
| 0.814 | 22.792000460 | 276207.294 | 2946211.136 |
| 0.815 | 22.820000460 | 276546.615 | 2949830.560 |
| 0.816 | 22.848000460 | 276885.936 | 2956449.984 |
| 0.817 | 22.876000460 | 277225.257 | 2957069.408 |
| 0.818 | 22.904000460 | 277564.578 | 2960688.832 |
| 0.819 | 22.932000460 | 277903.899 | 2964308.256 |
| 0.820 | 22.960000460 | 278243.220 | 2967927.680 |
| 0.821 | 22.988000460 | 278582.541 | 2971547.104 |
| 0.822 | 23.016000460 | 278921.862 | 2975166.528 |
| 0.823 | 23.044000460 | 279261.183 | 2978785.952 |
| 0.824 | 23.072000460 | 279600.504 | 2982405.376 |
| 0.825 | 23.100000460 | 279939.825 | 2986024.800 |
| 0.826 | 23.128000460 | 280279.146 | 2989644.224 |
| 0.827 | 23.15600046 | 280618.467 | 2993263.648 |
| 0.828 | 23.184000460 | 280957.788 | 2996883.072 |
| 0.829 | 23.212000460 | 281297.109 | 3000502.496 |
| 0.830 | 23.240000460 | 281636.430 | 3004121.920 |
| 0.831 | 23.268000470 | 284975.751 | 3007741.344 |
| 0.832 | 23.296000470 | 282315.072 | 3011360.768 |
| 0.833 | 23.324000470 | 282654.393 | 3014980.192 |
| 0.834 | 23.352000470 | 282993.714 | 3018599.616 |
| 0.835 | 23.380000470 | 283333.035 | 3022219.040 |
| 0.836 | 23.408000470 | 283672.356 | 3025838.464 |
| 0.837 | 23.436000470 | 284001.677 | 3029457.868 |
| 0.838 | 23.464000470 | 284350.998 | 3033077.312 |
| 0.839 | 23.492000470 | 284690.319 | 3036696.736 |
| 0.840 | 23.520000470 | 285029.640 | 3040316.160 |
| 0.841 | 23.548000470 | 285368.981 | 3043935.584 |
| 0.842 | 23.576000470 | 285708.282 | 3047555.008 |
| 0.843 | 23.604000470 | 286047.603 | 3051174.432 |
| 0.844 | 23.632000470 | 286386.924 | 3054793.856 |
| 0.845 | 23.660000470 | 286726.245 | 3058413.280 |
| 0.846 | 23.688000470 | 287065.566 | 3062032.704 |
| 0.847 | 23.716000470 | 287404.887 | 3065652.128 |

TABLE 3-continued

| | | | | | | | | |
|---|---|---|---|---|---|---|---|---|
| 0.848 | 23.744000470 | 287744.208 | 3069271.552 | | 0.928 | 25.984000520 | 314889.888 | 3358825.472 |
| 0.849 | 23.772000480 | 288083.529 | 3072890.976 | | 0.929 | 26.012000520 | 315229.209 | 3362444.896 |
| 0.850 | 23.800000480 | 288422.850 | 3076510.400 | | 0.930 | 26.040000520 | 315568.530 | 3366064.320 |
| 0.851 | 23.828000480 | 288762.171 | 3080129.824 | | 0.931 | 26.068000520 | 315907.851 | 3369683.744 |
| 0.852 | 23.856000480 | 289101.492 | 3083749.248 | | 0.932 | 26.096000520 | 316247.172 | 3373303.168 |
| 0.853 | 23.884000480 | 289440.813 | 3087368.672 | | 0.933 | 26.124000520 | 316586.493 | 3376922.592 |
| 0.854 | 23.912000480 | 189780.134 | 3090986.096 | | 0.934 | 26.152000520 | 316925.814 | 3380542.016 |
| 0.855 | 23.940000480 | 290119.455 | 3094607.520 | | 0.935 | 26.180000520 | 317265.135 | 3384161.440 |
| 0.856 | 23.968000480 | 290458.776 | 3098226.944 | | 0.936 | 26.208000520 | 317604.456 | 3387780.864 |
| 0.857 | 23.996000480 | 290798.097 | 3101846.368 | | 0.937 | 26.236000520 | 317943.777 | 3391400.288 |
| 0.858 | 24.024000480 | 291137.418 | 3105465.792 | | 0.938 | 26.264000530 | 318283.098 | 3395019.712 |
| 0.859 | 24.052000480 | 291478.739 | 3109085.216 | | 0.939 | 26.292000530 | 318622.419 | 3398639.136 |
| 0.860 | 24.080000480 | 291816.060 | 3112704.640 | | 0.940 | 26.320000530 | 318961.740 | 3402258.560 |
| 0.861 | 24.108000480 | 292155.381 | 3116324.064 | | 0.941 | 26.348000530 | 319301.061 | 3405877.984 |
| 0.862 | 24.136000480 | 292494.702 | 3119943.488 | | 0.942 | 26.376000530 | 319640.382 | 3409497.408 |
| 0.863 | 24.164000480 | 292834.023 | 3123562.912 | | 0.943 | 26.404000530 | 319979.703 | 3413116.832 |
| 0.864 | 24.192000480 | 293173.344 | 3127182.336 | | 0.944 | 26.432000530 | 320319.024 | 3416736.256 |
| 0.865 | 24.220000480 | 293512.665 | 3130801.760 | | 0.945 | 26.460000530 | 320658.345 | 3420355.680 |
| 0.866 | 24.248000480 | 293851.986 | 3134421.184 | | 0.946 | 26.488000530 | 320997.666 | 3423975.104 |
| 0.867 | 24.276000490 | 294191.307 | 3138040.608 | | 0.947 | 26.516000530 | 321336.987 | 3427594.528 |
| 0.868 | 24.304000490 | 294530.828 | 3141660.032 | | 0.948 | 26.544000530 | 321686.308 | 3431213.952 |
| 0.869 | 24.332000490 | 294869.949 | 3145279.456 | | 0.949 | 26.572000530 | 322015.629 | 3434833.376 |
| 0.870 | 24.360000490 | 295209.270 | 3148898.88 | | 0.950 | 26.600000530 | 322354.950 | 3438452.800 |
| 0.871 | 24.388000490 | 295548.591 | 3152518.304 | | 0.951 | 26.628000530 | 322694.271 | 3442072.224 |
| 0.872 | 24.416000490 | 295887.912 | 3156137.728 | | 0.952 | 26.656000530 | 323033.592 | 3445691.648 |
| 0.873 | 24.444000490 | 296227.233 | 3159757.152 | | 0.953 | 26.684000530 | 323372.913 | 3449344.072 |
| 0.874 | 24.472000490 | 296566.554 | 3163378.576 | | 0.954 | 26.712000530 | 323712.234 | 3452930.496 |
| 0.875 | 24.500000490 | 296905.875 | 3166996.000 | | 0.955 | 26.740000530 | 324051.555 | 3456549.920 |
| 0.876 | 24.528000490 | 297245.196 | 3170615.424 | | 0.956 | 26.768000540 | 324390.876 | 3460169.344 |
| 0.877 | 24.556000490 | 297584.517 | 3174234.848 | | 0.957 | 26.796000540 | 324730.197 | 3463788.768 |
| 0.878 | 24.584000490 | 297923.838 | 3177854.272 | | 0.958 | 26.824000540 | 325069.518 | 3467408.192 |
| 0.879 | 24.612000490 | 298263.159 | 3181473.696 | | 0.959 | 26.885200054 | 325408.839 | 3471027.616 |
| 0.880 | 24.620000490 | 298602.480 | 3185093.120 | | 0.960 | 26.880000540 | 325748.160 | 3474647.040 |
| 0.881 | 24.668000490 | 298941.801 | 3188712.544 | | 0.961 | 26.908000540 | 326087.481 | 3478268.464 |
| 0.882 | 24.696000490 | 299281.122 | 3192331.968 | | 0.962 | 26.936000540 | 326426.802 | 3481885.888 |
| 0.883 | 24.724000490 | 299620.443 | 3195951.392 | | 0.963 | 26.964000540 | 326766.123 | 3485505.312 |
| 0.884 | 24.752000500 | 299959.764 | 3199570.812 | | 0.964 | 29.992200054 | 327105.440 | 3489124.736 |
| 0.885 | 24.780000500 | 300299.085 | 3203190.240 | | 0.965 | 27.020000540 | 327444.765 | 3492744.160 |
| 0.886 | 24.808000500 | 300638.406 | 3206809.664 | | 0.966 | 27.048000540 | 327784.086 | 3496363.584 |
| 0.887 | 24.836000500 | 300977.727 | 3210429.088 | | 0.967 | 27.076000540 | 328123.407 | 3499983.008 |
| 0.888 | 24.864000500 | 301317.048 | 3214048.512 | | 0.968 | 27.104000540 | 328462.728 | 3503602.432 |
| 0.889 | 24.892000500 | 301656.369 | 3217667.936 | | 0.969 | 27.132000540 | 328802.049 | 3507221.856 |
| 0.890 | 24.920000500 | 301995.690 | 3221287.360 | | 0.970 | 27.160000540 | 329141.370 | 3510841.280 |
| 0.891 | 24.948000500 | 302335.011 | 3224906.784 | | 0.971 | 27.188000540 | 329480.691 | 3514460.704 |
| 0.892 | 24.976000500 | 302674.332 | 3228526.208 | | 0.972 | 27.216000540 | 329820.012 | 3518080.128 |
| 0.893 | 25.004000500 | 303013.653 | 3232145.632 | | 0.973 | 27.244000540 | 330159.333 | 3521699.552 |
| 0.894 | 25.032000500 | 303352.974 | 3235765.056 | | 0.974 | 27.272000550 | 330498.654 | 3525318.976 |
| 0.895 | 25.060000500 | 303692.295 | 3239384.480 | | 0.975 | 27.300000055 | 330837.975 | 3528938.400 |
| 0.896 | 25.088000500 | 304031.616 | 3243003.904 | | 0.976 | 27.328000550 | 331177.296 | 3532557.824 |
| 0.897 | 25.113000500 | 304370.937 | 3246823.328 | | 0.977 | 27.356000550 | 331516.617 | 3536177.248 |
| 0.898 | 25.144000500 | 304710.258 | 3260242.752 | | 0.978 | 27.384000550 | 331655.380 | 3539796.672 |
| 0.899 | 25.172000500 | 305049.579 | 3253862.176 | | 0.979 | 27.412000550 | 332195.259 | 3543416.096 |
| 0.900 | 25.200000500 | 305388.900 | 3257481.6 | | 0.980 | 27.440000550 | 332534.58 | 3547035.520 |
| 0.901 | 25.228000500 | 305728.221 | 3261101.024 | | 0.981 | 27.468000550 | 332873.901 | 3550654.944 |
| 0.902 | 25.256000510 | 206067.542 | 3264720.448 | | 0.982 | 27.496000550 | 333213.222 | 3557274.368 |
| 0.903 | 25.284000510 | 306406.863 | 3268339.872 | | 0.983 | 27.524000550 | 333552.543 | 3557893.732 |
| 0.904 | 25.312000510 | 306746.184 | 3271959.296 | | 0.984 | 27.552000550 | 333891.864 | 3561513.216 |
| 0.905 | 25.310000510 | 307085.505 | 3275578.720 | | 0.985 | 27.580000550 | 334231.185 | 3595132.640 |
| 0.906 | 25.368000510 | 307424.826 | 3279198.144 | | 0.986 | 27.608000550 | 334570.506 | 3568752.064 |
| 0.907 | 25.396000510 | 307764.147 | 3282817.568 | | 0.987 | 27.636000550 | 334909.827 | 3572371.488 |
| 0.908 | 25.424000510 | 308103.468 | 3286436.992 | | 0.988 | 27.66400055 | 335249.148 | 3575990.912 |
| 0.909 | 25.452000510 | 308442.789 | 3290056.416 | | 0.989 | 27.692000550 | 335588.469 | 3579610.336 |
| 0.910 | 25.480000510 | 308782.110 | 3293675.840 | | 0.990 | 27.720000550 | 335927.790 | 3683229.760 |
| 0.911 | 25.508000510 | 309121.431 | 3297295.264 | | 0.991 | 27.748000550 | 336267.111 | 3586849.184 |
| 0.912 | 25.536000510 | 309460.752 | 3300914.688 | | 0.992 | 27.776000560 | 336606.432 | 3590495.608 |
| 0.913 | 25.584000510 | 309800.073 | 3304534.112 | | 0.993 | 27.804000560 | 336945.753 | 3594088.032 |
| 0.914 | 25.592000510 | 310139.394 | 3308453.536 | | 0.994 | 27.832000560 | 337285.074 | 3597707.456 |
| 0.915 | 25.820000510 | 310478.715 | 3311772.960 | | 0.995 | 27.860000560 | 337624.395 | 3901326.880 |
| 0.916 | 25.648000510 | 310818.036 | 3315392.384 | | 0.996 | 27.888000560 | 337963.716 | 3604946.304 |
| 0.917 | 25.676000510 | 311157.357 | 3319011.808 | | 0.997 | 27.916000580 | 338303.037 | 3608568.728 |
| 0.918 | 25.704000510 | 311496.878 | 3322631.232 | | 0.998 | 27.944000560 | 338642.358 | 3612185.152 |
| 0.919 | 25.732000510 | 311835.999 | 3326250.656 | | 0.999 | 27.972000560 | 338981.679 | 3615804.586 |
| 0.920 | 25.780000520 | 312175.320 | 3329870.080 | | 1.000 | 28.000000560 | 339321.000 | 3619424.000 |
| 0.921 | 25.788000520 | 312514.641 | 3333489.504 | | 1.001 | 28.02800056 | 339660.321 | 3623043.424 |
| 0.922 | 25.816000520 | 312853.962 | 3337108.928 | | 1.002 | 28.056000560 | 339999.642 | 3626662.848 |
| 0.923 | 25.844000520 | 313193.283 | 3340728.352 | | 1.003 | 28.084000560 | 340338.963 | 3630282.272 |
| 0.924 | 25.872000520 | 313532.604 | 3344347.776 | | 1.004 | 28.11200056 | 340676.284 | 3633880.400 |
| 0.925 | 25.900000520 | 313871.925 | 3347967.200 | | 1.005 | | 341017.605 | 3637521.120 |
| 0.926 | 25.928000520 | 314211.246 | 3351586.324 | | 1.006 | | | 3641140.544 |
| 0.927 | 25.956000520 | 314550.567 | 3355206.048 | | 1.007 | | | 3644759.968 |

TABLE 3-continued

| | |
|---|---|
| 1.008 | 3648379.392 |
| 1.009 | 3651998.816 |

The treatment has been verified by laboratory testing. Preliminary studies were conducted using eight (8) anesthetized dogs. Each dog was intravenously administered 30 mg/Kg of Na-pentobarbital. The heart rates in the anesthetized state averaged 120-170 beats per minute. The baseline measurements of the heart rates were made from recordings of standard electrocardiograms. Cardiac conduction measurements were made from an His bundle electrogram. This His bundle electrogram shows conduction time from the upper chambers of the heart (the atria, A) to the beginning of electrical activation (His bundle, H) of the lower chambers (ventricles). The A-to-H interval measures conduction time in milliseconds through the A-V node.

The control measurements are recorded. Both heart rate and A-V nodal conduction are consistently depressed by parasympathetic nerve stimulation. Electromagnetic fields are positioned for parasympathetic nerve stimulation by either of two methods: 1) a Helmholtz coil, five-cent size, surrounding the vago-sympathetic trunk dissected from the aortic sheath in the neck, or 2) via a larger, 18 inch diameter Helmholtz coil situated on either side of the dog's chest.

Once the control measurements are recorded, the system 25 is applied for treatment. A dog was placed between the first coil 31 and the second coil 33. The first coil 31 and the second coil 33 each have a diameter of eighteen inches (18 in) and are arranged in the familiar Helmholtz coil arrangement. The well-known Helmholtz coil configuration has two loops as shown in FIG. 1. A Helmholtz coil is a device that produces a highly uniform magnetic field in a space d between the first coil 35 and the second coil 37. See ROALD K. WANGSNESS, ELECTROMAGNETIC FIELDS 234 (1986).

The first coil 35 is positioned on one side of the dog's chest and the second coil 37 is positioned on an opposite side of the dog's chest. This arrangement aligns the dog's heart along a common axis $L_1$-$L_1$. The signal generator 27 used in the experiments is a Stanford Research System model D-360 ultra low distortion function generator. The Stanford Research System is capable of producing a frequency adjustable and an amplitude adjustable sinusoidal, rectilinear, triangular, or trapezoidal waveform input signal.

Field strengths applied were from nanogauss range to microgauss range in cardiovascular studies. Specific electromagnetic fields were selected on the basis of Jacobson Resonance ($mc^2 = Blvq$). The critical molecules were: acetylcholine; epinephrine; nor-epinephrine; serotonin; cytokines; interferon; vaso-interstinal peptide; protons; electrons; muons; mesons; and photons—sub-atomic species. Sinusoidal waves were commonly used, although rectilinear waves also provided advantages.

The attenuated signal from the voltage attenuator 31 is applied to the first coil 35 and the second coil 37 for thirty five (35) minutes. Spontaneous heart rate was initially measured. The A-H interval was measured during atrial pacing at a constant heart rate for three periods: prior to application of the electromagnetic radiation, during the application of the electromagnetic radiation, and for three (3) hours after the 35 minute application of the electromagnetic field. Measurements were also made with stepwise increase in the two forms of the parasympathetic nerve stimulation mentioned above.

While the signal generator 27, the voltage attenuator 31, and the at least one inductor are shown as connected by wires, those skilled in the art recognize any means of transmitting signals between electrical components can be used. Copper or aluminum lines, circuit boards, infrared signals, or any other portion of the electromagnetic spectrum may be used to transmit signals between components.

Figure 2:
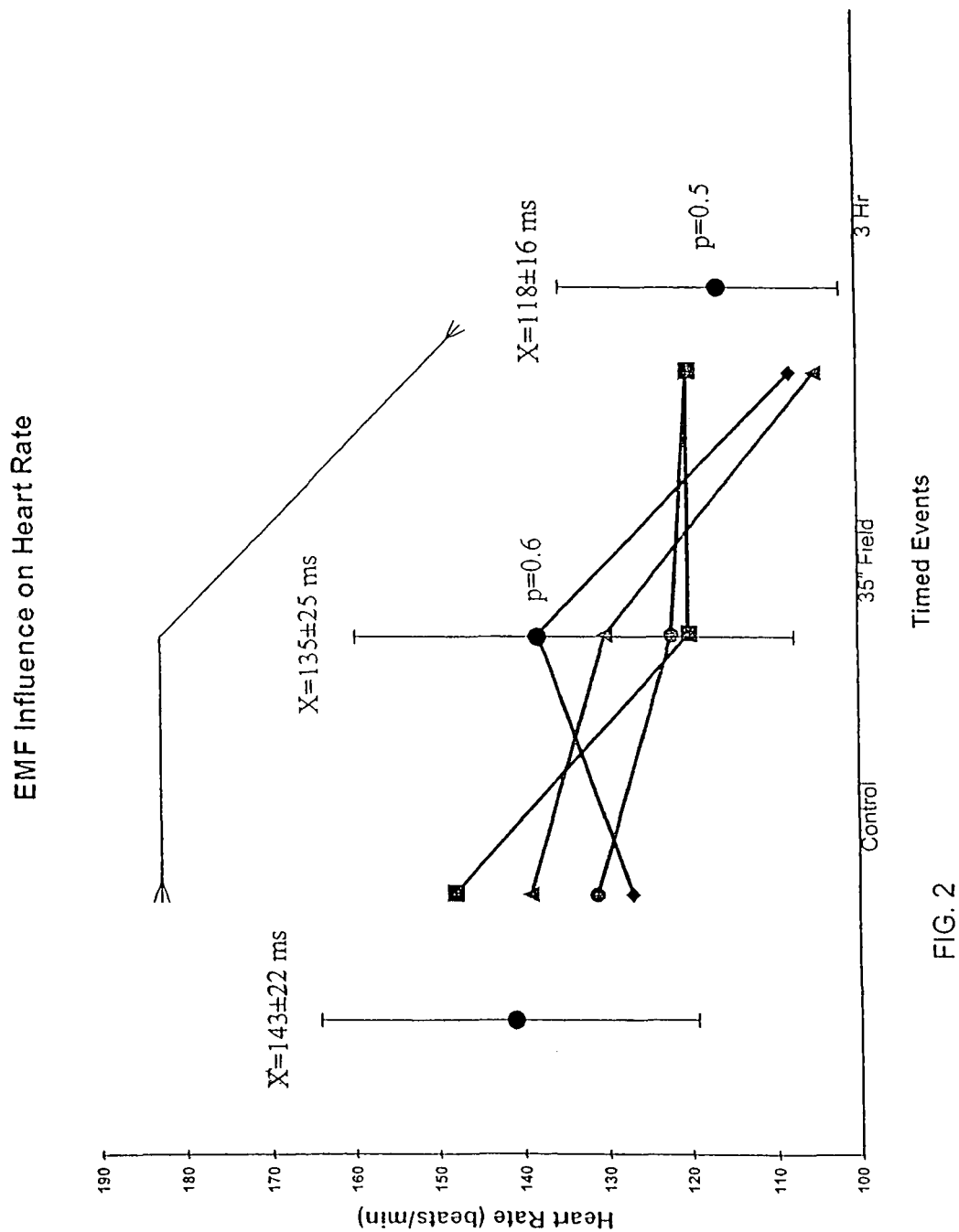
FIGS. 2 and 3 are graphs showing the results of the very low frequency treatment.
Figure 3:
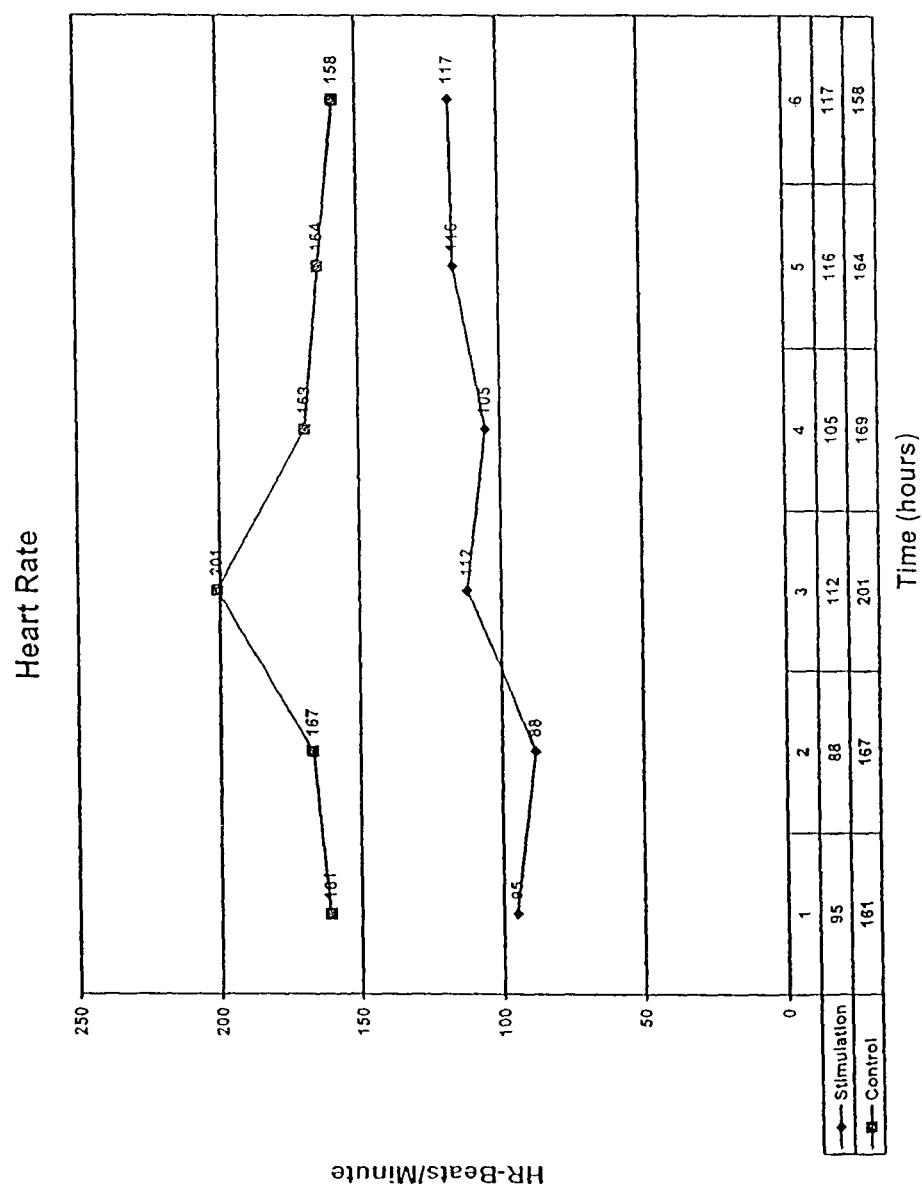

FIGS. 2 and 3 graphically show the results of the very low frequency treatment. FIG. 2 is a graph showing each dog's heart rate during three (3) hours after application of the electromagnetic radiation. FIG. 3 shows each dog's heart rate in a sham control test with no application of electromagnetic radiation. As FIG. 2 shows, there is a significant trend during the three (3) hours for a reduction of the spontaneous heart rate and for a reduction of the heart rate. This trend is not significant at thirty five (35) minutes, when the electromagnetic radiation is initially terminated. Heart rates, however, significantly decrease at three (3) hours. FIG. 3, conversely, shows the results for the sham control during spontaneous rhythm and with electrical stimulation over a period of six (6) hours. No electromagnetic radiation is applied during the sham control, and FIG. 3 shows no trend for either an increase or a decrease in heart rate during this period.

Figure 4:
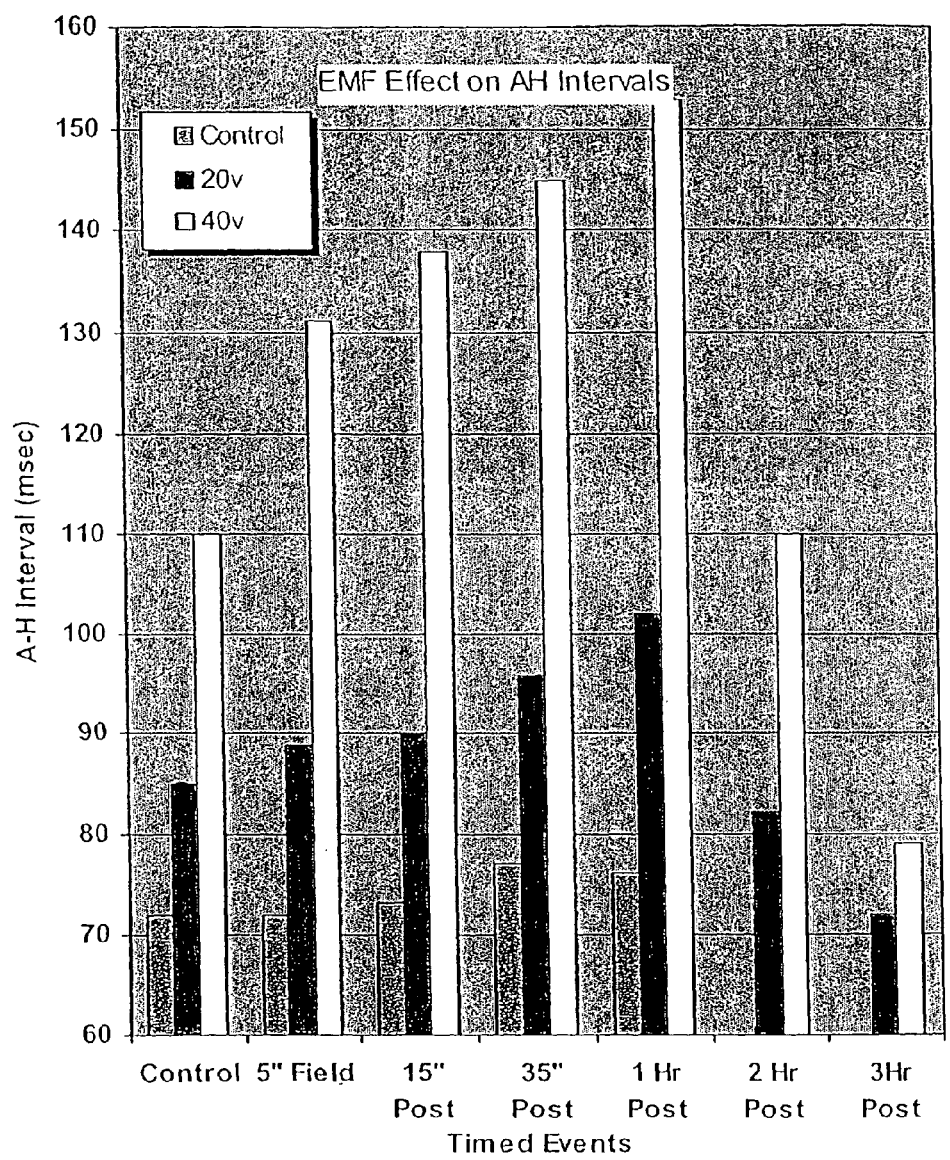
FIG. 4 is a graph showing the effects of the treatment on atrioventricular conduction measured as A-H intervals.

FIG. 4 graphically shows the effects of the treatment on A-H intervals. The time for each dog's A-H interval was measured during and at several periods after the electromagnetic field application. Three autonomic nerve stimulation levels were also tested: forty volts (40V), twenty volts (20V), and a control no stimulation level. The rate of change of A-H prolongation or slowing of A-V conduction for one (1) to three (3) hours was greatest at the highest level (40V) of stimulation. The induction of A-V block, i.e., atrial activation not followed by ventricular activation, more interestingly occurred at the highest stimulation level (again, 40V) at two (2) and three (3) hours even though other values, of autonomic nerve stimulation were returning to control levels at three (3) hours.

These results were admittedly tempered in two dogs. One dog showed a significant increase in heart rate associated with the application of electromagnetic radiation. Another dog showed no change over the three (3) hour period. The results of these two dogs suggest perhaps both the parasympathetic arm (slowing heart rate and A-V conduction) and the sympathetic arm (speeding heart rate and A-V conduction) arm of the autonomic nervous system could be activated by low frequency electromagnetic radiation. A balance between the parasympathetic and the sympathetic systems could result in no change in heart rate and A-V conduction; whereas, a greater sympathetic effect can induce a speeding of heart rate and A-V conduction.

The parasympathetic effect is well known to predominate. Six (6) of the eight (8) dogs, as mentioned above, experienced parasympathetic slowing of heart rate and of A-V conduction. This parasympathetic effect is pronounced despite the use of Na-pentobarbital as the anesthesia. Na-pentobarbital usually affects the parasympathetic system and tends to enhance a sympathetic tone. An increased heart rate, therefore, is usually experienced when Na-pentobarbital is administered. These results, however, are due to the greater effect of the electromagnetic field on enhancing the parasympathetic slowing of heart rate. This parasympathetic slowing of heart rate has also been seen in human patients exposed to the same low-frequency electromagnetic radiation.

The most direct application of the treatment is to slow heart rate. The low-frequency electromagnetic treatment activates parasympathetic neurotransmitters. This activation of parasympathetic neurotransmitters induces slowing of the heart rate. If a patient has supraventricular tachycardias, such as the most common atrial fibrillation with a rapid ventricular response, the non-invasive application of low-frequency electromagnetic treatment could exert control over the heart rate. This treatment could provide acute control and longer term period control. This control over heart rate would be especially useful for treatment of intensive care patients, with concomitant atrial fibrillation and poor left ventricular function, in whom inotropic drugs, such as dopamine, would exacerbate rapid ventricular response. Drugs, such as beta-blockers and calcium channel blockers, would tend to slow ventricular response, but, could also exacerbate heart failure and further cardiac decompensation. Cardioversion would require ventricular compromising anesthetics and, despite multiple conversions by shocks to the heart, many patients quickly revert to atrial fibrillation.

The treatment may also be applied for chronic uses. The low-frequency electromagnetic treatment could be used to provide long-term "toning" of the parasympathetic nervous system. This toning is very useful in patients with low heart rate variability. The effects of increased parasympathetic tone has been shown to be cardio-protective in myocardial infarction survivors by increasing heart rate variability. This therapeutic modality could be used as an adjunctive measure in patients with implantable cardioverter defibrillation ("ICD") to reduce shock episodes. This would require the addition of a coil configuration to the implanted electrode catheter. Specifically, the coil for "toning" the parasympathetic nervous system could be built as part of the catheter which lies in the superior vena cava adjacent to the parasympathetic nerve. This therapeutic modality could be applicable to ICD patients with and without beta-blockers. This addition would considerably enhance patients acceptance of ICD implantation, and significantly add to the quality of life subsequently.

The above described in vivo testing of low-frequency electromagnetic treatment in dogs suggests that similar results may be found in humans.

FIG. 5 is an isometric view of a catheter 41 for invasively administering the low-frequency electromagnetic treatment. The catheter 41 includes a catheter 43. The catheter 43 is a tubular passage member 45 defining a longitudinal axis $L_2$-$L_2$. The longitudinal axis $L_2$-$L_2$ is bounded by an enclosing wall 47 to define a cross-section of the tubular passage member 45 that is transverse to the longitudinal axis $L_2$-$L_2$. The tubular passage member 45 may include a cap portion 49. The cap portion 49 is at a distal end of the tubular passage member 45, and the cap portion 49 securely engages the tubular passage member 49. At least one inductor is contained within a bore 51 of the catheter tube 43. The inductor is shown in FIG. 5 as the first coil 35. The first coil 35 is serially arranged with the second coil 37 to produce the Helmholtz coil arrangement. As discussed previously, other coil arrangements may be substituted for the Helmholtz coil arrangement, such as solenoid or saddle coils. A first wire 53 is shown connecting the first coil 35 to a first terminal 55. This first terminal 55 receives the attenuated signal from the voltage attenuator (shown as reference numeral 31 in FIG. 1), and the attenuated signal flows through the first wire 53 and to the first coil 35. The first wire 53 connects at one end to the first coil 35, passes through the bore 51, and connects at an opposite end to the first terminal 55. A second wire 57 connects at one end to the second coil 37, passes through the bore 51, and connects at an opposite end to a second terminal 59. The second terminal 59 is connected to the signal generator 27 to complete the circuit.

The catheter 41 can be used to administer the low-frequency electromagnetic treatment. The catheter 41 is inserted into the patient and positioned proximate a region of treatment. Once the catheter 41 is positioned, the attenuated signal is sent from the voltage attenuator 31 to the at least one inductor. The attenuated signal flows through the at least one inductor and produces the magnetic flux density. The locally positioned catheter 41 can thus locally impinge the electromagnetic field within the patient. The catheter 41 allows the parasympathetic and sympathetic effects of the low-frequency electromagnetic field treatment to be focused on particular regions, or even particular organs, of the patient. The catheter 41, for example, could be positioned in a target region of the superior vena cava region ("SVC") at the azagous vein junction. This particular region of treatment could interventionally reduce or increase the heart rate and the conduction rate, depending on stimulation of parasympathetic or sympathetic nervous innervation to the heart, respectively.

As would be understood by one of ordinary skill in the art, the catheter 41 can have a variety of configurations. Although the catheter 41 is shown as having a generally longitudinal shape, the catheter 41 may have any curvature desired to suit a particular application. One, two, three, or any number of lumina could be added for particular operations or applications. The catheter 41 may also include any number of ports for irrigation or suction. The specific size of the catheter 41 may be simply determined without undue experimentation. The size of the catheter 41 or any lumen may be varied to the natural conformation of the region to be treated or of the insertion passage.

One of ordinary skill in the art would recognize that the catheter 43 can also be made from a variety of materials. The catheter 43 is preferably made from a plastic material. The plastic material should have enough rigidity to be inserted into a patient, but the plastic material should also be flexible to conform to the curvature of blood vessels and organs. A guide wire may even be used to advance the catheter for selective positioning. The catheter 43 could be produced by extruding rigid polyvinyl chloride with appropriate melt characteristics for bending. Other materials include more traditional high density polyethylene, low density polyethylene, and low density polypropylene compounds.

The bore 51 of the catheter 41 can be filled with a variety of fluids. The bore 51, for example, may be exposed at a proximate end to atmospheric conditions. The bore 51, alternatively, could be filled with water, saline, dissolved oxygen, or carbon dioxide. Magneto-rheological fluids would be especially advantageous to further locally adjust the electromagnetic radiation. Any fluid compatible with the patient and with the application could be used in the bore.

FIG. 6 includes two partial views of an alternative embodiment of the catheter 41 for invasively administering the low-frequency electromagnetic treatment. This catheter 41, however, includes a balloon tip 61. FIG. 6A shows the balloon tip 61 in a deflated condition, while FIG. 6B shows the balloon tip 61 in an inflated condition. The balloon tip 61 is attached to a distal end of the catheter tube 43. The balloon tip 61 is sealed to the catheter tube 43, and an interior region 63 of the balloon tip 61 communicates with the bore 51 of the catheter tube 43. The balloon tip 61 is inflatable and deflatable in response to fluid pressure within the bore 51. The balloon tip 61, for example, may be inflated by atmospheric conditions, water, saline, dissolved oxygen, carbon dioxide, or any other fluid compatible with the patient and with the application.

The balloon tip 61 contains at least one inductor. While the inductor is shown as the first coil 35 and the serially-connected second coil 37, the inductor could include other coil arrangements discussed previously, such as solenoid or saddle coils. The inductor is preferably small in size such that insertion of the catheter 41 into the patient is not hindered or complicated. The inductor could correspondingly expand and contract with the balloon.

The first coil 35 and the second coil 37, in this embodiment, are preferably constructed of thin wire. The first coil 35 and the second coil 37 could be molded within a wall of the balloon tip 61, or the thin wire coils could be attached to the wall of the balloon tip 61. As fluid pressure within the bore 51 causes the balloon tip 61 to inflate, the first coil 35 and the second coil 37 would correspondingly expand and contract with the balloon.

Figure 7:
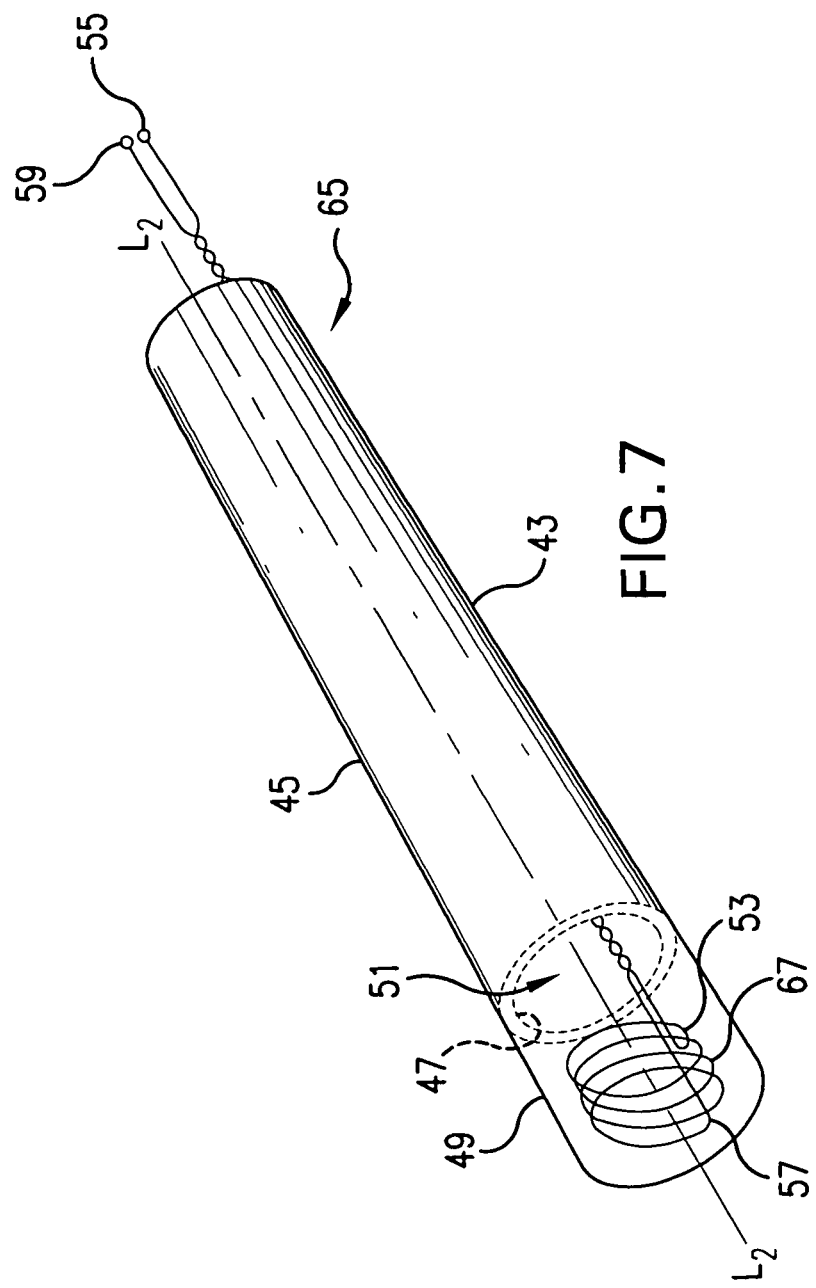
FIG. 7 is an isometric view of another alternative embodiment of a catheter for invasively administering the very low frequency electromagnetic treatment.

FIG. 7 is also an isometric view of an alternative embodiment of a catheter 65 for invasively administering the low-frequency electromagnetic treatment. This catheter 65, however, includes a solenoidal coil arrangement 67. While the solenoidal coil arrangement 67 is shown as having four (4) coils, those skilled in the art recognize the solenoidal coil arrangement 67 may consist of any number N of coils. The non-infinite length of the solenoidal coil 67, and the non-closely wound coils, ensures a constant current will produce magnetic flux density outside of the solenoidal coil arrangement 67. See DAVID K. CHENG, FIELD AND WAVE ELECTROMAGNETICS 231 (1983). The solenoidal coil arrangement 67 is connected at one end to the first wire 53, and the solenoidal coil arrangement 67 is connected at another end to the second wire 57. The catheter 65, for example, could be positioned in a target region of the SVC in the proximity of the azagous vein junction. This particular region of treatment could tone the parasympathetic nerves to the heart in patients with previous myocardial infarction ("MCI"). The treatment could prevent ventricular tachycardia and ventricular fibrillation, since enhanced parasympathetic tone has been shown to be protective against these malignant arrhythmias.

Figure 8:
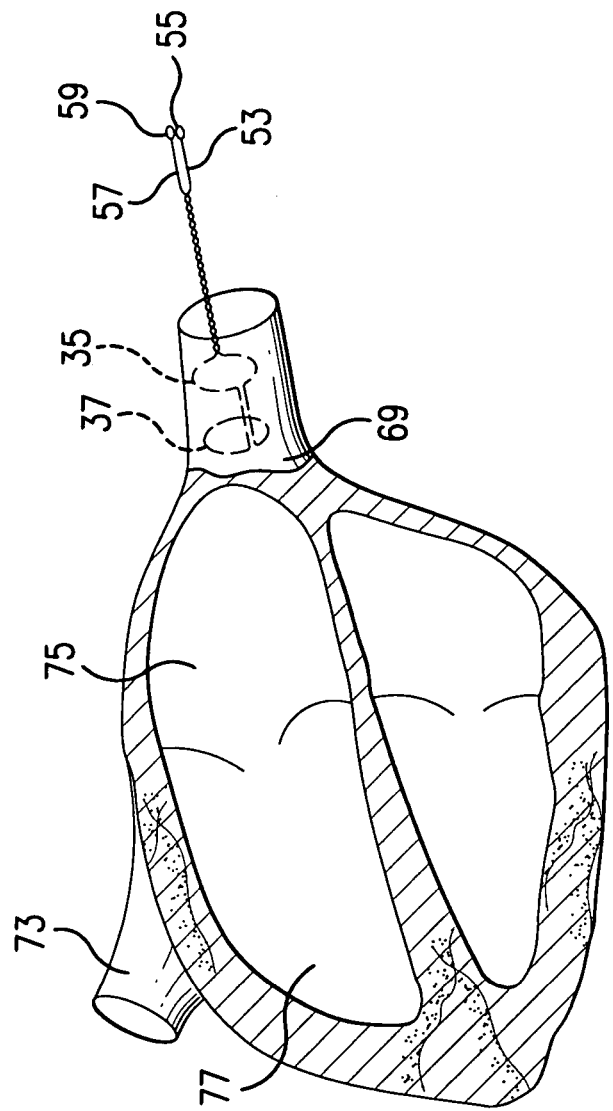
FIG. 8 shows an implantable device for invasively administering the very low frequency electromagnetic treatment.

FIG. 8 shows an implantable inductor for invasively administering the low-frequency electromagnetic treatment. The implantable inductor is shown as the first coil 35 and the serially-connected second coil 37 implanted proximate the superior vena cava region 69 of a human heart 71. The inferior vena cava region 73, the right atrium region 75, and the right ventricle region 77 are shown for orientation and clarity. While the inductor is shown as the first coil 35 and the serially-connected second coil 37, the inductor could include other coil wire arrangements, such as saddle or solenoid coil arrangement (such as shown and discussed as reference numeral 67 in FIG. 7). The inductor is implantable for prevention of ventricular tachycardia by toning of the parasympathetic nerves. The Helmholtz coil arrangement of the first coil 35 and the serially-connected second coil 37, for example, could be positioned in a target region of the right ventricle. The treatment could prevent ventricular tachycardia and ventricular fibrillation in patients at risk for sudden death syndrome, due to life threatening ventricular arrhythmias.

Because the inductor is implantable, the electromagnetic treatment can be programmable. The signal generator (shown as reference numeral 27 in FIG. 1) would also advantageously be implantable, and the signal generator could be programmed to periodically, randomly, or even on-command supply the input signal. A sensor could even monitor parasympathetic conditions and automatically activate the signal generator. The low-frequency electromagnetic treatment can thus be applied when needed. The treatment could also be applied on-command if, for instance, the signal generator is wirelessly commanded to produce the input signal.

Figure 9:
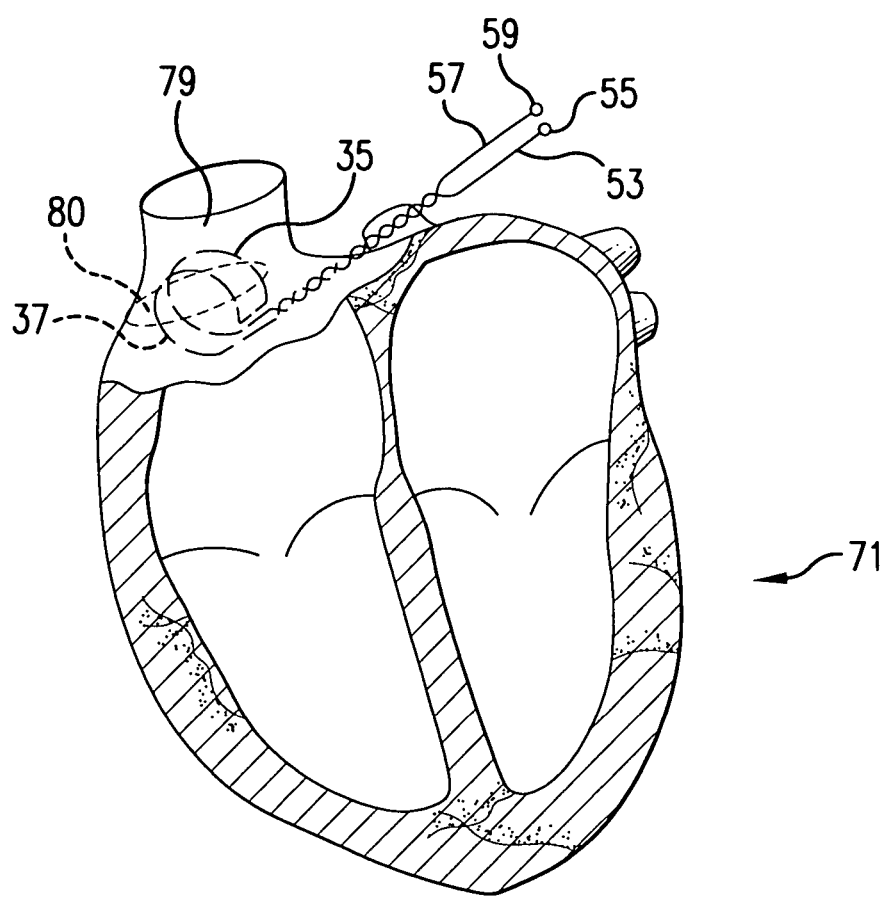
FIG. 9 shows an alternative application for an implantable device for invasively administering the very low frequency electromagnetic treatment.

FIG. 9 shows an alternative application for the implantable inductor. The inductor is again shown as the Helmholtz coil arrangement of the first coil 35 and the second coil 37, although alternative coil arrangements may be used, such as solenoid or saddle coils. The inductor is shown implanted so as to surround the sino-atrial node region 79 of the dog heart 71. The sino-atrial location of the inductor focuses the treatment directly on parasympathetic nerve elements at the sino-atrial node. Also, the low-frequency electromagnetic treatment, for example, may be focused on the right and left cervical vago-sympathetic nerve trunk. The low-frequency electromagnetic treatment predominantly activates the parasympathetic arm of the autonomic nervous system, and thereby can slow heart rate, A-V conduction, and reduce the rate of sinus tachycardia.

Figure 10:
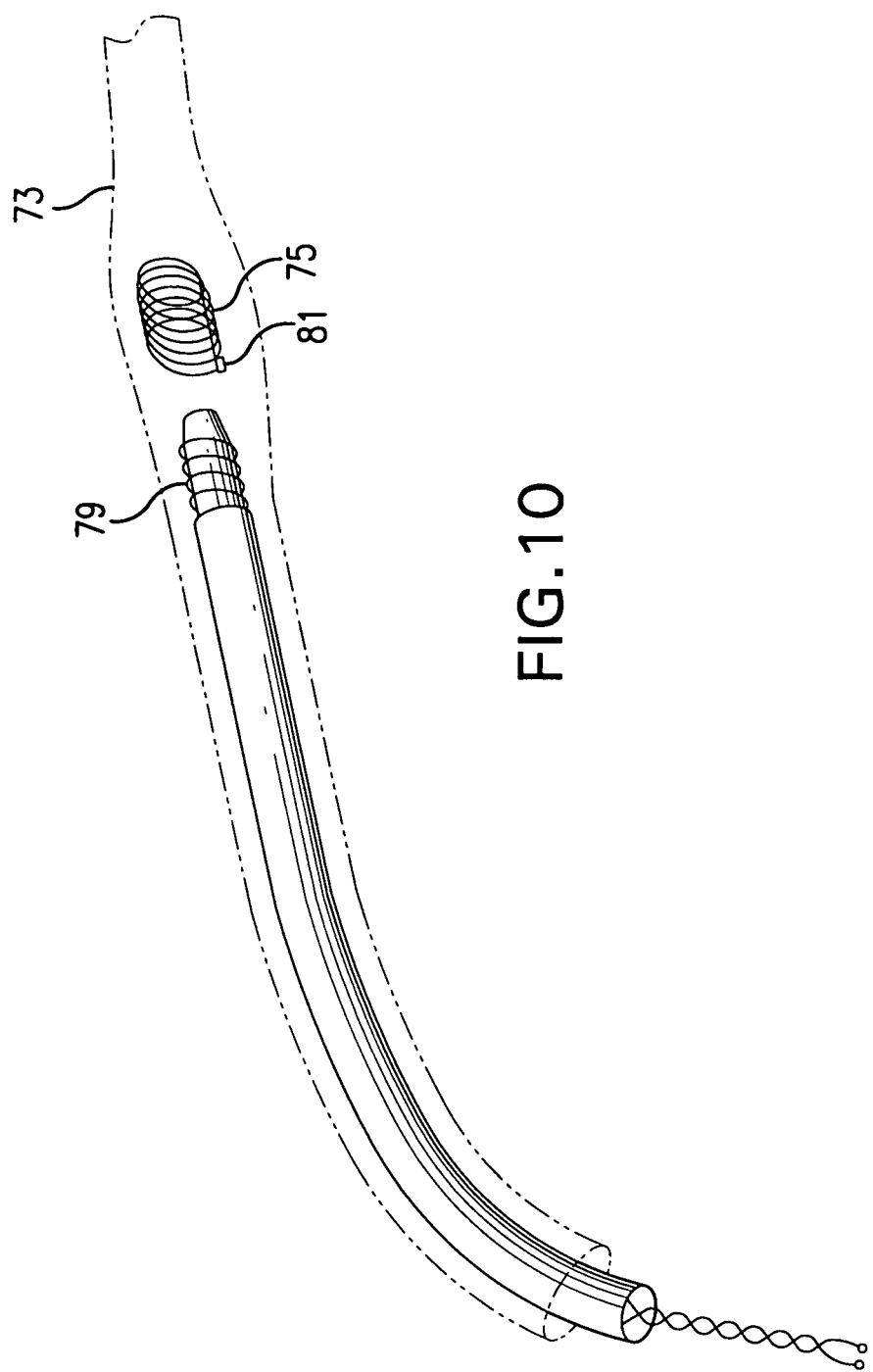
FIG. 10 shows still another alternative embodiment for invasively administering electromagnetic treatment referred to herein as a stent coil. A signal is induced in the stent coil by a catheter coil.

FIG. 10 also shows an alternative embodiment for invasively administering the low-frequency electromagnetic treatment. A stent coil 75 is implanted in the blood vessel 73. The stent coil 75 is a solenoid wire coil arrangement that is implantable in a blood vessel 73. As would be recognized by one of ordinary skill in the art, the stent coil arrangement may be implanted by standard medical devices. The coil has a capacitor 81 attached to one end such that the solenoid 75 and the capacitor 81 are connected in series. The solenoid 75 and the capacitor 81 thus form what is commonly referred to in the art as an "LC" circuit ("L" representing the inductor and "C" representing the capacitor.) As would be known by one of ordinary skill in the art, an undriven current generated through an LC circuit will oscillate in amplitude. If there were no resistance in the LC circuit, the current would continue to oscillate indefinitely. However, there is some resistance in the LC circuit because current through a wire inherently has some resistance. The resistance of the wire has a dampening effect on the current oscillation. As with any solenoid or other wire arrangement, the oscillation of a current through the inductor coil 75 induces a magnetic field. Although the stent coil has been described as being a solenoid, other shapes to generate the field desired can be used. For example, a saddle coil may suffice.

A current may be generated in the inductor coil 75 using two methods. The first method is illustrated in FIG. 10. As shown in FIG. 10, a catheter 77 has a solenoid coil arrangement 79 attached to one end as shown in FIG. 10. The catheter is a vascular access device that is able to be inserted into the blood vessel 73. The coil 79 of wire is attached to a generator (not shown) by wires 71. The generator sends a current through the wires 71 and the coil 79.

The catheter coil 79 is insertable into the stent coil 75. As would be understood by one of ordinary skill in the art, if the catheter coil 79 is inserted into the stent coil 75, a current running through the catheter coil 79 will induce a current in the stent coil 75. As discussed previously, a current generated in the stent coil 75 will oscillate because the solenoid stent coil 75 and the capacitor 81 form an LC circuit. Oscillation of current amplitude is a commonly known property of LC circuits. The current in the stent coil 75 will continue to oscillate after the catheter is removed, subject to the dampening factor caused by resistivity of the wire forming the coil 75 and the capacitor 81.

The current oscillation in the stent coil 75 induces an electromagnetic field in the center of and around the stent coil 75. Thus, the stent coil 75 applies an electromagnetic field locally to the patient or organism in which the stent coil 75 is implanted. The stent coil 75 continues to apply the electromagnetic field after the catheter coil 77 is removed from insertion within the stent coil 75.

Figure 11:
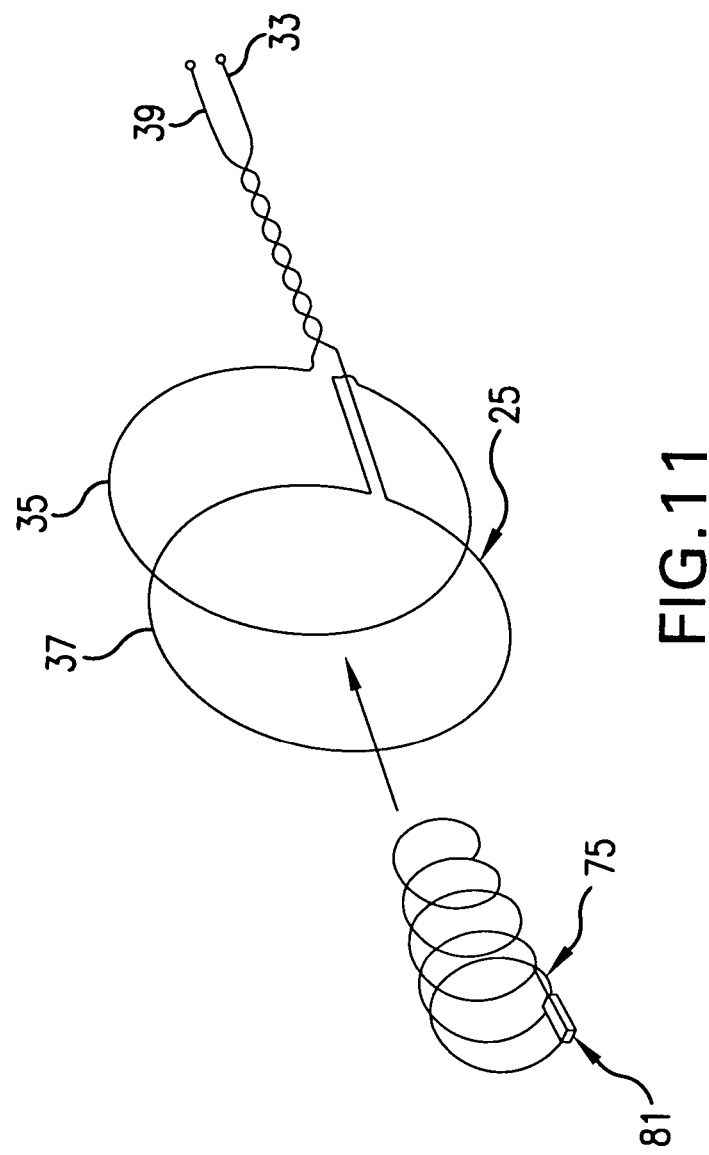
FIG. 11 shows the stent coil configured such that a signal is induced in the stent coil by an external coil arrangement.

The second method of generating a current through the stent coil 75 is shown in FIG. 11. The stent coil 75 and microchip capacitor 81 are inserted or implanted into an area of an organism such as a blood vessel in the same configuration shown in FIG. 10. The organism or patient in which the stent coil 75 has been implanted is then exposed to an electromagnetic field generated by an external coil configuration. The electromagnetic field may be generated by a Helmholtz coil configuration 25 as shown in FIG. 10. As described previously, the Helmholtz coil configuration has a first coil 35 arranged in series with a second coil 37, which is connected to a signal generator by two wires 39 and 33. As would be readily understood by one of ordinary skill in the art, other coil configurations for generating an electromagnetic field may be easily substituted for the Helmholtz coil 25 arrangement shown in FIG. 11. Examples of such alternative coil arrangements include solenoid coils and saddle coils with one or more coils of a shape such that a magnetic field is induced through the coil.

The patient or organism in which that stent coil 75 has been implanted is placed within the magnetic field produced by the coil arrangement 25. As with the configuration shown in FIG. 10, the external magnetic field induces a current through the stent coil 75, which oscillates subject to a dampening factor. As would be understood by one of ordinary skill in the art, the current oscillation continues after the external magnetic field is removed.

While the present invention has been described with respect to various features, aspects, and embodiments, those skilled and unskilled in the art will recognize the invention is not so limited. Other variations, modifications, and alternative embodiments may be made without departing from the spirit and scope of the present invention.

What is claimed is:

1. A method of treating the heart in an organism, the method comprising:
   (a) providing an organism to be treated;
   (b) determining that an electromagnetic field having a flux density that is specific to only sympathetic stimulation should be applied to the organism;
   (c) delivering the magnetic flux density specific to sympathetic stimulation to the organism or part of the organism, wherein the magnetic flux is between $7.5 \times 10^{-8}$ gauss to about $1 \times 10^{-6}$ gauss, and wherein the magnetic flux density (B) for the electromagnetic field to be applied to the organism is determined using the formula $mc^2 = Bvlq$, wherein m equals a mass of one or more biological targets related to cardiac function; c equals the speed of light; v equals the inertial velocity of said mass in at least one of the earth's orbital or earth's rotational systems; l equals the length of the organism to which the field will be applied; and q equals unity of charge and has a value of 1 ab-coulomb, and wherein the frequency (f) for each flux value ranges from 0 to 28 Hertz (Hz), and wherein the target is one of a nerve growth factor (NGF), a homeobox, a neurotransmitter, a cytokine, a motor protein, a structural protein, kinesine, microtubule associated protein (MAP), spectrin, brain specific fodrin, neurofilaments, tubulin, platelet derived growth factor (PDGF), vasointestinal peptide, epinephrine, serotonin, acetylcholine, tubulin subunits, or adenosine; and
   (d) determining that the treatment increases heart rate and/or decreases A-H intervals in the organism's heart.

2. The method of claim 1, wherein said subjecting the organism or the part of the organism to the electromagnetic field further comprises placing the organism inside an external apparatus for generating the electromagnetic field.

3. The method of claim 1, wherein said subjecting the organism or the part of the organism to the electromagnetic field further comprises implanting a device for generating the electromagnetic field in the organism, wherein the apparatus is implanted in proximity to the organism's heart, and wherein the device comprises an inductor operatively connected to a capacitor for generating the electromagnetic field.

4. The method of claim 1, wherein the organism is one having a diseased state or condition which is at least one of irregular heart rate, elevated blood pressure, cardiovascular failure, blood clots, atrial fibrillation, ventricular fibrillation, atrioventricular blockage, diseased heart valves, enlarged heart, circulatory blockage, coronary insufficiencies, or ischemia.

5. The method of claim 3, wherein the inductor comprises a Helmholtz coil, a solenoid coil, or a saddle coil.

6. The method of claim 3, wherein the device comprises a catheter or stent for implanting the device in the organism.

7. The method of claim 3, wherein the device comprises a signal generator for generating an electric signal and an attenuator.

8. The method of claim 7, wherein signal generator is external to the organism.

* * * * *